(12) United States Patent
Wang et al.

(10) Patent No.: US 8,361,021 B2
(45) Date of Patent: Jan. 29, 2013

(54) SYSTEM FOR REDUCING AIR BUBBLES IN A FLUID DELIVERY LINE

(75) Inventors: David T. Wang, Sunnyvale, CA (US); Robert P. Cousineau, Boston, MA (US); Lori E. Lucke, Eagan, MN (US); Marwan A. Fathallah, Mundelein, IL (US); John Stephen Ziegler, Arlington Heights, IL (US)

(73) Assignee: Hospira, Inc., Lake Forest, IL (US)

( * ) Notice: Subject to any disclaimer, the term of this patent is extended or adjusted under 35 U.S.C. 154(b) by 120 days.

(21) Appl. No.: 13/154,674

(22) Filed: Jun. 7, 2011

(65) Prior Publication Data

US 2011/0238013 A1     Sep. 29, 2011

Related U.S. Application Data

(62) Division of application No. 12/194,685, filed on Aug. 20, 2008, now Pat. No. 7,981,082.

(60) Provisional application No. 60/957,024, filed on Aug. 21, 2007.

(51) Int. Cl.
*A61M 1/00* (2006.01)

(52) U.S. Cl. ........ 604/122; 604/123; 604/124; 604/125; 73/861.21; 73/861.05; 73/861.06

(58) Field of Classification Search .......... 604/122–125; 73/861.21, 861.05–861.06
See application file for complete search history.

(56) References Cited

U.S. PATENT DOCUMENTS

| | | |
|---|---|---|
| 3,974,683 A | 8/1976 | Martin |
| 4,265,240 A | 5/1981 | Jenkins |
| 4,280,495 A | 7/1981 | Lampert |
| 4,292,405 A | 9/1981 | Mascoli |
| 4,298,357 A | 11/1981 | Pernic |
| 4,324,662 A | 4/1982 | Schnell |
| 4,366,384 A | 12/1982 | Jensen |
| 4,379,452 A | 4/1983 | DeVries |
| 4,399,362 A | 8/1983 | Cormier et al. |
| 4,453,931 A | 6/1984 | Pastrone |
| 4,521,212 A | 6/1985 | Ruschke |
| 4,637,813 A | 1/1987 | DeVries |
| 4,658,244 A | 4/1987 | Meijer |
| 4,781,687 A | 11/1988 | Wall |
| 4,789,014 A | 12/1988 | DiGianfilippo |
| 4,828,693 A | 5/1989 | Lindsay |
| 4,927,411 A | 5/1990 | Pastrone et al. |
| 4,936,820 A | 6/1990 | Dennehey |
| 4,981,467 A | 1/1991 | Bobo, Jr. et al. |
| 5,102,392 A | 4/1992 | Sakai et al. |
| 5,116,316 A | 5/1992 | Sertic |
| 5,158,441 A | 10/1992 | Aid |
| 5,174,472 A | 12/1992 | Raque et al. |
| 5,176,631 A | 1/1993 | Koenig |
| 5,180,287 A | 1/1993 | Natwick et al. |
| 5,191,795 A | 3/1993 | Fellingham et al. |
| 5,192,340 A | 3/1993 | Grant et al. |

(Continued)

OTHER PUBLICATIONS

Written Opinion and Search Report for corresponding International Application No. PCT/us08/73828, Apr. 11, 2008.

*Primary Examiner* — Kevin C Sirmons
*Assistant Examiner* — Edelmira Bosques
(74) *Attorney, Agent, or Firm* — Michael R. Crabb

(57) ABSTRACT

A method and pump that accurately senses air in a fluid delivery line pulses or activates and deactivates the air sensor (s) multiple times during the pumping phase of the fluid delivery cycle and can generate alarms based upon a single indication or a cumulative indication of air in the line. The pump can include multiple air sensors spaced along the delivery line so that the method can use the multiple signals therefrom to distinguish real moving air bubbles from false positives and/or air bubbles adhered to the inner wall of the line.

6 Claims, 8 Drawing Sheets

U.S. PATENT DOCUMENTS

| | | |
|---|---|---|
| 5,200,090 A | 4/1993 | Ford |
| 5,207,642 A | 5/1993 | Orkin |
| 5,232,476 A | 8/1993 | Grant |
| 5,244,568 A | 9/1993 | Lindsay |
| 5,308,333 A | 5/1994 | Skakoon |
| 5,319,979 A | 6/1994 | Abrahamson |
| 5,343,885 A | 9/1994 | Grant |
| 5,382,232 A | 1/1995 | Hague et al. |
| 5,421,208 A | 6/1995 | Packard |
| 5,496,273 A | 3/1996 | Pastrone et al. |
| 5,554,115 A | 9/1996 | Thomas et al. |
| 5,583,280 A | 12/1996 | Mo et al. |
| 5,616,124 A | 4/1997 | Hague et al. |
| 5,630,710 A | 5/1997 | Tune |
| 5,658,133 A | 8/1997 | Anderson et al. |
| 5,800,387 A | 9/1998 | Duffy et al. |
| 5,843,035 A | 12/1998 | Bowman et al. |
| 5,906,598 A | 5/1999 | Giesler |
| 5,927,349 A | 7/1999 | Martucci |
| 5,938,634 A | 8/1999 | Packard |
| 5,954,696 A | 9/1999 | Ryan |
| 6,003,388 A | 12/1999 | Oeftering |
| 6,017,493 A | 1/2000 | Cambron |
| 6,027,441 A | 2/2000 | Cantu |
| 6,033,561 A | 3/2000 | Schoendorfer |
| 6,068,612 A | 5/2000 | Bowman et al. |
| 6,110,153 A | 8/2000 | Davis |
| 6,142,008 A | 11/2000 | Cole et al. |
| 6,168,561 B1 | 1/2001 | Cantu |
| 6,192,752 B1 | 2/2001 | Blaine |
| 6,202,711 B1 | 3/2001 | Martucci |
| 6,203,528 B1 | 3/2001 | Deckert |
| 6,261,065 B1 | 7/2001 | Nayak |
| 6,398,760 B1 | 6/2002 | Danby |
| 6,408,679 B1 | 6/2002 | Kline-Schroeder et al. |
| 6,457,346 B1 | 10/2002 | Kline-Schroeder et al. |
| 6,463,785 B1 | 10/2002 | Kline-Schroeder et al. |
| 6,467,331 B1 | 10/2002 | Kline-Schroeder et al. |
| 6,475,178 B1 | 11/2002 | Krajewski et al. |
| 6,481,980 B1 | 11/2002 | Vandlik |
| 6,489,896 B1 | 12/2002 | Platt et al. |
| 6,494,694 B2 | 12/2002 | Lawless et al. |
| 6,531,708 B1 | 3/2003 | Malmstrom |
| 6,629,449 B1 | 10/2003 | Kline-Schroeder et al. |
| 6,716,004 B2 | 4/2004 | Vandlik |
| 6,759,007 B1 | 7/2004 | Westberg |
| 6,814,547 B2 | 11/2004 | Childers |
| 6,846,161 B2 | 1/2005 | Kline |
| 6,852,094 B2 | 2/2005 | Beck |
| 6,929,751 B2 | 8/2005 | Bowman |
| 6,932,114 B2 | 8/2005 | Sparks |
| 6,984,218 B2 | 1/2006 | Nayak et al. |
| 7,104,763 B2 | 9/2006 | Bouton et al. |
| 7,258,534 B2 | 8/2007 | Fathallah et al. |
| 7,360,999 B2 | 4/2008 | Nelson et al. |
| 7,556,616 B2 | 7/2009 | Fathallah et al. |
| 2001/0015099 A1 | 8/2001 | Blaine |
| 2002/0173703 A1 | 11/2002 | Lebel et al. |
| 2004/0158193 A1 | 8/2004 | Bui et al. |
| 2005/0209563 A1 | 9/2005 | Hopping et al. |
| 2005/0214129 A1 | 9/2005 | Greene et al. |
| 2007/0058412 A1 | 3/2007 | Wang et al. |

SYSTEM FOR REDUCING AIR BUBBLES IN A FLUID DELIVERY LINE

CROSS-REFERENCE TO RELATED APPLICATIONS

This application is a divisional application of U.S. application Ser. No. 12/194,685, filed on Aug. 20, 2008 now U.S. Pat. No. 7,981,082, entitled "System and Method for Reducing Air Bubbles in a Fluid Delivery Line", which is incorporated herein by reference in its entirety. This application claims priority based upon U.S. Provisional Application Ser. No. 60/957,024 filed Aug. 21, 2007, which is expressly incorporated herein by reference in its entirety.

FEDERALLY SPONSORED RESEARCH OR DEVELOPMENT

None.

TECHNICAL FIELD

The invention relates to medical pumps for delivering a substance, such as a fluid to a patient. In particular, the present invention relates to detection of air in a fluid delivery line, such as within a line set, used with a medical pump, which reduces and/or prevents the creation of air bubbles within the fluid delivery line.

BACKGROUND OF THE INVENTION

Modern medical care often involves the use of medical pump devices to deliver substances, such as fluids and/or fluid medicine to patients. Medical pumps permit the controlled delivery of substances to a patient, and such pumps have largely replaced gravity flow systems, primarily due to the pump's much greater accuracy in delivery rates and dosages, and due to the possibility for flexible yet controlled delivery schedules.

A typical positive displacement pump system includes a pump device driver and a disposable fluid or pumping chamber, defined in various forms including but not limited to a cassette, syringe barrel or section of tubing. A disposable cassette, which is adapted to be used only for a single patient and for one fluid delivery round, is typically a small plastic unit having an inlet and an outlet respectively connected through flexible tubing to the fluid supply container and to the patient receiving the fluid. The cassette includes a pumping chamber, with the flow of fluid through the chamber being controlled by a plunger or pumping element activated in a controlled manner by the device driver.

For example, the cassette chamber may have one wall or wall portion formed by a flexible, resilient diaphragm or membrane that is reciprocated by the plunger and the driver to cause fluid to flow. The pump driver device includes the plunger or pumping element for controlling the flow of fluid into and out of the pumping chamber in the cassette, and it also includes control mechanisms to assure that the fluid is delivered to the patient at a pre-set rate, in a pre-determined manner, and only for a particular pre-selected time or total dosage.

The fluid enters the cassette through an inlet and is forced through an outlet under pressure. The fluid is delivered to the outlet when the pump plunger forces the membrane into the pumping chamber to displace the fluid. During the intake stroke the pump plunger draws back, the membrane covering the pumping chamber pulls back from its prior fully displaced configuration, and the fluid is then drawn through the open inlet and into the pumping chamber. In a pumping stroke, the pump plunger forces the membrane back into the pumping chamber to pressurize and force the fluid contained therein through the outlet. Thus, the fluid flows from the cassette in a series of spaced-apart pulses rather than in a continuous flow.

A fluid delivery line, such as a polymer tube which is well known in the art, is used with the medical pump devices to deliver the fluid from a fluid reservoir to the patient, such as through a catheter or needle connected to the fluid delivery line. In one prior medical pump, the medical pump included an air sensing arrangement having a transmitter and receiver for sensing air and/or air bubbles in the fluid delivery line. The transmitter is positioned within the pump at a location which is adjacent to a first side of the fluid delivery line when the fluid delivery line has been installed or mounted by a caregiver within the medical pump device. The receiver is positioned within the pump at a location which is adjacent to a second and opposite side of the fluid delivery line to the first side when the fluid delivery line has been installed or mounted by a caregiver within the medical pump device. The transmitter transmits an ultrasonic signal which travels through the fluid delivery line, and which is received by the receiver on the opposite side of the fluid delivery line from the transmitter. The signal transmitted by the transmitter and received by the receiver is modified or affected by the physical elements (the fluid delivery line, air within the fluid delivery line, fluid within the fluid delivery line, etc.) the signal encounters between the transmitter and the receiver.

In one medical pump system, disclosed in U.S. Pat. No. 6,142,008 to Cole et al., which is hereby incorporated by reference herein, while a motor actuates a pumping cassette, a controller controls the sampling by an air bubble sensor over a portion of the fluid delivery line. The controller determines whether each sample is either 100% air or 100% liquid by comparing a sampled signal from air bubble sensor to a predetermined threshold that is a fixed percentage of a last reading that was found to indicate the presence of liquid in fluid delivery line. If the sampled signal is valid and below the predetermined threshold, the controller determines that the sample indicates the presence of air. Conversely, if a valid sampled signal is above the predetermined threshold, the controller determines that the sample indicates the presence of a liquid in the distal tubing. The controller accumulates the volume associated with each sample as delta values used to determine the total liquid volume and the total air volume.

In this medical pump system, each sample is a representative approximation of the unsampled portion of distal tubing that precedes the current sampling, and the air sampling time intervals approximate the unsampled time intervals. The controller must determine a sampling time interval (in seconds) for continuous rotation of motor using a ratio of the motor's output drive shaft. For example, if the pumping cassette is pumping at high rates (e.g., 1000 ml/hr) and the sampling time interval is less than 40 milliseconds, the controller must set the sampling time interval, for example to 40 milliseconds. Further, if the pumping cassette is pumping at low rates (e.g., less than 126 ml/hr), the sampling time interval is set at 32 milliseconds, based on the ratio and other factors. Ideally, the sampling time interval begins when valves in the pumping cassette open and the interval ends when the valves close.

In this medical pump system, the controller turns off the power to air bubble sensor when the motor is not actuating the pumping cassette. In other words, the controller shuts down power to the air bubble sensor between each actuation of the pumping cassette, but leaves power to the air bubble sensor on during the actuation. When controller turns the power on to air bubble sensor, just prior to actuation beginning, approximately one millisecond of warm up time is needed before the sensor may be used. The controller checks the output signal from air bubble sensor for a false high when the associated amplification electronics are first turned on and when the transmitter of the air bubble sensor is not transmitting an ultrasonic pulse to the receiver of the air bubble sensor.

Equations are employed by controller for various functions, as described in this patent, including control of air bubble sensor, such as determining an air bubble sensor sampling rate, which is dependent on the flow rate and other variables. In addition, various logic flows are used to detect air in the fluid delivery line, and provide alarms when sufficient air is detected in the fluid delivery line. However, these equations and logic flows are based on a theory of operation which keeps the air bubble sensor powered on during the entire non-retraction portion or pressurization phase of each stroke.

Thus, it is a principal object of this invention to provide a medical pump and a method of operating a medical pump to overcome these deficiencies. The present invention is provided to solve the problems discussed above and other problems, and to provide advantages and aspects not provided by prior medical pumps.

As such, one object of the present invention includes reducing nuisance alarms.

One further object includes reducing dancing bubbles potentially resulting from ultra-sonic waves passing through the fluid delivery line, by reducing the amount of air detection sensor usage during pump operation, while at the same time providing for reliable air detection within the fluid delivery line.

One additional object includes reducing dancing bubbles potentially resulting from ultra-sonic waves passing through the fluid delivery line, by reducing the amount of air detection sensor usage during the delivery phase of pump operation, while at the same time providing for reliable air detection within the fluid delivery line.

One further object includes reducing bubble generation and/or small bubble accumulation/conglomeration potentially resulting from ultra-sonic waves passing through the fluid delivery line, by reducing the amount of air detection sensor usage during pump operation while at the same time providing for reliable air detection within the fluid delivery line.

One additional object includes reducing bubble generation and/or small bubble accumulation/conglomeration potentially resulting from ultra-sonic waves passing through the fluid delivery line, by reducing the amount of air detection sensor usage during the delivery phase of pump operation while at the same time providing for reliable air detection within the fluid delivery line.

One further object includes establishing robustness in the method and system of air detection using at least predetermined, adaptive and/or dynamic threshold selection according to empirical testing and/or delivery conditions at the time of actual delivery (i.e. tube type, fluid used, temperature, etc.)

One additional object includes intelligent and/or adaptive placement (when/where) of the first and subsequent air detection sensor "ping(s)" based times and/or angles of rotation (hard times and/or angles, and/or delays from a reference points) for one or more pumping mechanisms.

One further object includes using existing pump hardware technology and updating the software code to implement the system and method of the present invention.

One additional object includes reducing nuisance alarms resulting from dancing bubbles by, for example, using multiple air detection sensors to detect air bubbles in the fluid delivery line.

A full discussion of the features and advantages of the present invention is deferred to the following summary, detailed description, and accompanying drawings.

SUMMARY OF THE INVENTION

The present invention is directed to a medical pump with an improved method for detecting air in a fluid delivery line using a medical pump having a first air detection sensor with a first transmitter and a first receiver. In one embodiment, the medical pump also has a second air detection sensor with a second transmitter and a second receiver. Both the first and second sensors are provided for sensing whether there is air in the fluid delivery line and the amount of air in the fluid delivery line. As described in greater detail herein, one embodiment of the medical pump is provided in connection with a disposable pumping chamber, such as a cassette or tube, for delivering a substance, such as a fluid, to a patient. The medical pump further includes a pump drive for exerting a force on the pumping chamber to apply pressure on the substance. The medical pump also includes a pump drive position sensor operatively connected to the pump drive for continuously sensing the position of the pump drive. The medical pump further has a processor or processing unit in electronic communication with the pump drive, the pump drive position sensor and the first air detection sensor for providing control of these elements and for receiving input information to utilize in making various determinations and operating the medical pump as provided herein. The medical pump further has a memory in electronic communication with the processor. The memory can have stored therein programming code for execution by the processor. The programming code, at least in part, generally carries out the method of the present invention.

In one embodiment, the method, and medical pump, includes starting a fluid delivery cycle. Once the fluid delivery cycle begins, the medical pump activates or provides power to the first air detection sensor after a first predetermined cycle parameter value has been met. This and other predetermined cycle parameter values can be an amount of time that has passed after the stroke cycle has begun, can be an angular distance that the pump drive has traveled, can be a linear distance that the pumping chamber has moved, and/or some other time, distance or other parameter which spaces the activation of the sensor from the beginning of the stoke cycle or from some other reference point. In one embodiment, each fluid delivery cycle or stroke includes a pressurization phase, a pumping phase, and a retraction phase, as will be described in greater detail below. The medical pump then measures a first air content signal which is generated by the first air detection sensor. When a second or plurality of air detection sensors are used, the medical pump will also measure a second or plurality of additional air content signals which are generated by the second or plurality of additional air detection sensors, although the measurements, detection and/or determinations for the second or plurality of additional air detection sensors may be performed after a predetermined or calculated (dynamic) delay, such as a time or distance delay. The medical pump then generates first (and second/a plurality of additional, when additional air detection sensors are present) air content data from the first (second/plurality of additional) air content signal(s), such as by converting an analog signal to a digital value or data representative of the signal measured by the air detection sensor. The processor can receive a plurality of samples for each of air content signals and convert each of the samples from an analog signal to a digital value. As used herein, the term signal can be singular or plural, and one of skill in the art should understand that the plurality of samples can be taken from a single signal or a plurality of signals, for example the same signal at different times, when reference is made to a "signal" or "signals." The processor can be arranged to average each of the samples for the measured first air signals. The processor then deactivates the first (second/a plurality of additional) air detection sensor after measuring the air content signal and after a second (third, etc., for the second, etc. air detection sensors) predetermined cycle parameter value has been met, such as a travel distance or time.

The medical pump further determines whether the air content data (or air detection data) has met a first predetermined air threshold. The processor sets the air in line counter to zero prior to measuring the first air content signal. In one embodiment, the first predetermined threshold being met represents that there is air in the fluid delivery line. If the first predetermined threshold is met, in one embodiment, the processor increments an air in line counter. In one embodiment, the size of the increment can be the stroke volume of one stoke of a pumping cycle divided by three. The processor further determines whether the air in line counter has met an alarm threshold, and issues an air in line alarm if the alarm threshold has been met. The alarm threshold can be set by the manufacturer at the factory and/or modified by a caregiver or biomedical engineer and/or can be configured as a downloadable drug library parameter that can be customized by the user for a particular clinical care area, pump type, pump software version, patient type (adult versus infant, for example), or drug. In another embodiment, if the first predetermined threshold is not met, the air in line counter is set to zero.

Within the same stroke, the processor reactivates the first (second/plurality of additional) air detection sensor(s) after a third (fourth, etc.) predetermined cycle parameter value has been met, such as a distance or time, as provided above, and as explained in greater detail below. The medical pump then measures a second air content signal generated by the first (second/plurality of additional) air detection sensor(s) and generates second air content data from the second air content signal(s) (for each air detection sensor), in a similar manner as the first air content signal(s). The processor further determines whether the second air content data (or air detection data) has met the first predetermined air threshold, and deactivates the first air detection sensor after measuring the second air content signal and after a fourth predetermined cycle parameter value has been met, such as a distance or time.

In one embodiment, the first and other predetermined cycle parameter values can be relative to the start of the fluid delivery cycle, such as a time since the beginning of the cycle or stroke, or such as a distance the pump drive has traveled since the beginning of the cycle or stroke. The second and other predetermined cycle parameter values can also be relative to the first and subsequent predetermined cycle parameter values or relative to when (a time) or to a where (a location) such values have been met.

In a further embodiment, the processor can control the pump drive to cause the pump drive to rotate or drive at a speed based on the delivery rate set by the caregiver. The delivery rate and pump drive speed establish a stroke speed. The number of samples measured and received by the medical pump is independent of the stroke speed. Thus, the way in which the measurements are taken, including the number of samples taken of the air content signal is not dependent on the speed of the fluid moving through the delivery line.

In an additional embodiment, the processor increments an air in line counter when the first predetermined threshold is met. If the first predetermined threshold is not met, the processor will set the air in line counter to zero. This determination of whether the first predetermined threshold is met continues in a programmed loop. Each time this determination is made the processor will store another air in line counter value representing a "current" value of the air in line counter, which is proximate to each time that the step of measuring the first air content signal occurs. Thus, a plurality of stored air in line counter values is created and stored. The processor further determines whether each of the plurality of stored air in line counter values has met a first predetermined air in line counter threshold. For each of the plurality of stored air in line counter values that has not met the first predetermined air in line counter threshold, the processor is arranged to set each such plurality of stored air in line counter values to zero.

The processor and programming code can also be arranged to establish a current cumulative air in line counter value. In one embodiment, the current cumulative air in line counter value is established by determining a highest stored air in line counter value for each group of continuous non-zero stored air in line counter values, and adding the highest stored air in line counter value to a previously determined cumulative air in line air counter value. The processor then determines if the current cumulative air in line counter value has met a cumulative air in line counter value threshold. If so, the processor issues a cumulative air in line alarm. This determination can be performed over a predetermined cumulative time interval. When the fluid delivery cycle begins, the predetermined cumulative time interval begins at the beginning of the fluid delivery cycle. Over time, the predetermined cumulative time interval shifts, with the oldest value dropping out when a new "current" value is determined and stored, in a "moving window" or first in/first out (FIFO) process.

As provided above, the medical pump can have additional air detection sensors downstream, or upstream, from the first air detection sensor along the fluid delivery line for detecting air in the fluid delivery line. When a second (or plurality of additional) air detection sensor(s) is used, after the first predetermined cycle parameter value has been met, the medical pump measures a first air content signal generated by the second (plurality of additional) air detection sensor(s). The processor and programming code running therein are configured to generate first air content data from the first air content signal generated by the second (plurality of additional) air detection sensor(s). When two air sensors are used, the processor is further configured to determine when the first air content signal generated by the first air detection sensor is measured to establish a first air detection time. The processor is also configured to determine when the first air content signal generated by the second air detection sensor is measured to establish a second air detection time, and to determine whether the difference between the second detection time and the first detection time has met a predetermined delay time. The predetermined delay time can be dependent upon a fluid delivery line size, a delivery rate, and/or a distance between the first air detection sensor and the second air detection sensor, as will be described greater detail herein. One of ordinary skill should understand that these principles and steps also apply to an embodiment where there are more than two air detection sensors as well. In one embodiment, the processor is configured to set the air in line counter to zero if the difference between the second detection time and the first detection time has not met the predetermined delay time.

Continuing with a two sensor embodiment, if the difference between the second detection time and the first detection time has met the predetermined delay time, the processor determines whether the difference between the second detection data has met/not met a predetermined multi-sensor tolerance value. When the predetermined multi-sensor tolerance value is not met, the processor is configured to increment an air in line counter, such by a stroke volume divided by three, similar to one prior embodiment. Also similar to one prior embodiment, the processor determines whether the air in line counter has met an alarm threshold, and issues an air in line alarm when the alarm threshold has been met.

In another embodiment, the processor is further configured to deactivate the second air detection sensor, after measuring the first content signal generated by the second air detection sensor, and after the second predetermined cycle parameter value has been met. After a third predetermined cycle parameter value has been met, the medical pump/processor are also configured to reactivate the second air detection sensor, measure a second air content signal generated by the second air detection sensor, and generate second air content data from the second air content signal generated by the second air detection sensor. After measuring the second air content signal generated by the second air detection sensor and after the fourth predetermined cycle parameter value has been met, the processor is configured to deactivate the second air detection sensor. The values of the third and fourth predetermined cycle parameter cause the second air content signal to be measured prior to the end of the pumping phase of the delivery cycle. Again, one of skill in the art should understand that these principles and steps also apply to embodiments which include more than two air detection sensors.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings.

DETAILED DESCRIPTION

Figure 1:
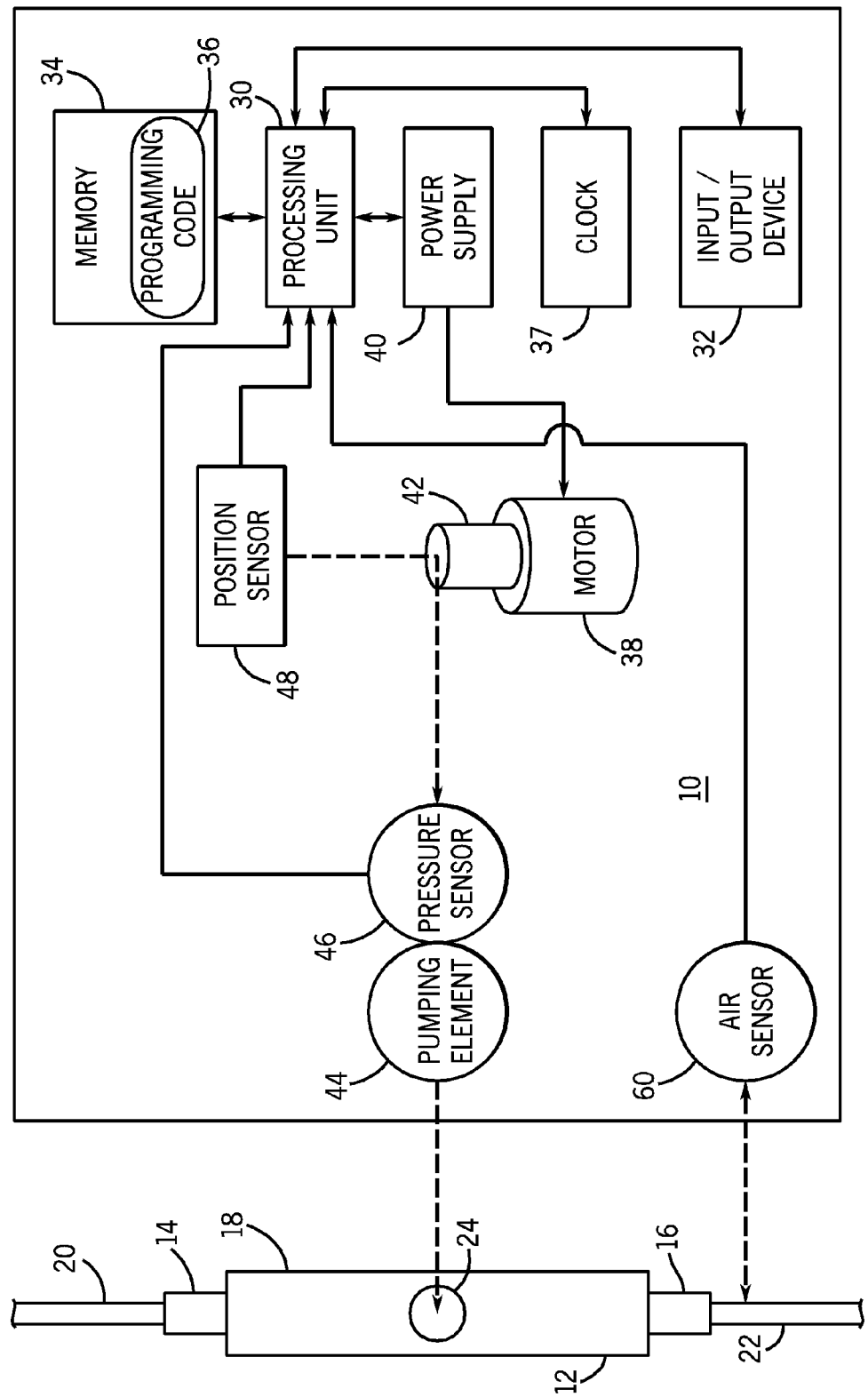
FIG. 1 is an illustration of one embodiment of a medical pump of the present invention, wherein a single air sensor is provided

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the invention to the embodiments illustrated.

A medical pump includes but is not limited to enteral pumps, infusion pumps, cassette pumps, syringe pumps, peristaltic pumps, or any positive displacement fluid pumping device for the delivery of fluids intravenously or intra-arterially to a patient. Referring initially to FIG. 1, one embodiment of a medical pump 10 is provided in connection with a disposable pumping chamber, such as a cassette 12 or tube, for delivering a substance, such as a fluid, to a patient. In various embodiments of the medical pump of the present invention, the pumping chamber is a portion of at least one of a cassette, a tube, and/or a syringe, depending on the type of medical pump. The medical pump 10 provides a mechanism for adjusting an actual delivery of the substance based on variations from nominal data used to estimate pump performance. A processing unit 30 is included in pump 10 and performs various operations described in greater detail below. An input/output device 32 communicates with the processing unit 30 and allows the user to receive output from processing unit 30 and/or input information or commands into the processing unit 30. Those of ordinary skill in the art will appreciate that input/output device 32 may be provided as a separate display device and/or a separate input device. A memory 34 communicates with the processing unit 30 and stores code and data necessary for the processing unit 30 to calculate and output the operating conditions of pump 10. The memory 34 stores a programming code 36 formed in accordance with the present invention for processing data to determine and control the operating condition of the medical pump 10. A clock 37 is used to keep time in the pump 10. The clock 37 is connected to the processing unit 30, and provides the processing unit 30 with time information for correlating data over time or conducting time sensitive activities. An electric motor 38 is controlled by processing unit 30 and is energized by a power supply 40 to serve as a prime mover for rotatably driving a shaft 42 connected to the motor 38. The processing unit 30 orders the motor 38 to run at a constant speed or at different speeds, depending on the motor being used and depending on the flow rate desired through the pump 10. The down-stroke or delivery portion of the stroke has the motor 38 running directly from power supply 40. The up-stroke, retract or fill portion of the stroke is run at a voltage set by the processing unit 30, so that the retract times are varied by the processing unit 30, where higher desired flow rates require faster retract speeds. A pumping element 44, such as a plunger, is operatively associated with the shaft 42. When energized, the pumping element 44 reciprocates back and forth to periodically down-stroke, causing pumping element 44 to press on pumping chamber 24, and expel fluid therefrom. On an up-stroke, pumping element 44 releases pressure from pumping chamber 24 and thereby draws fluid from inlet port 14 into pumping chamber 24. Thus, the pumping element 44 intermittently pressurizes the pumping chamber 24 during a pumping cycle. The power supply 40, the motor 38, and/or the pumping element 44 together, alone, or in some combination thereof, may be considered a pump drive for the purposes of the present specification.

The pump drive step value can be a time to drive the pump drive, a linear distance to drive the pump drive, an angular distance or degree for the pump drive to travel, and/or some other travel value. The motor can be driven at a constant rate or a variable rate. In one form of a medical pump 10 using a constant rate motor or motor drive, such a motor drive creates variable speed movement of the pumping element 44, such as a plunger, via a series of cams. However, as mentioned, a variable speed motor or motor drive may be used to create constant speed pumping element movement, such as a constant speed plunger. The calculations, determinations and delivery scheme will change accordingly, as one of ordinary skill in the art would understand. Other parts and/or elements may also make up the pump drive, as one of ordinary skill in the art would understand. In addition, parts of each of the power supply 40, the motor 38, the pumping element 44, and/or other elements can make up what is referred to herein as the pump drive, with the understanding that the pump drive is controlled by the processing unit 30 for driving the delivery of the substance to the patient through the use of the pumping chamber.

A force/pressure sensor 46 is operatively associated with the pumping element 44 to detect the force or pressure exerted by the pumping element 44 on the pumping chamber 24. As shown in FIG. 1, the sensor 46 can be directly connected to the pumping element and positioned in-line with the pumping element 44, between the pumping chamber 24 and the shaft 42 of the motor 38. In this embodiment, the sensor 46 is the only force/pressure sensor included in the medical pump 10, and operates to sense the force/pressure on pumping element 44 as well as to generate a force/pressure signal based on this force/pressure. The force/pressure sensor 46 is in electronic communication with the processing unit 30 to send the force/pressure signal to the processing unit 30 for use in determining operating conditions of pump 10. One of ordinary skill in the art will appreciate that the pressure sensor 46 may be a force transducer, strain gauge, or any other device that can operatively sense the pressure or related force brought to bear on the pumping chamber 24 by pumping element 44.

A position sensor 48 is operatively associated with the pumping element 44 to directly or indirectly detect the position of the pumping element 44. The position sensor 48 tracks each pumping cycle of pump 10 by detecting the position of the pumping element 44 at each position within each cycle. As shown, the position sensor 48 is associated with the shaft 42. The position sensor 48 generates a pump drive travel signal by detecting the rotational position of the shaft 42. The position sensor 48 is in electronic communication with the processing unit 30 to send the position signal to the processing unit 30. The processing unit 30 utilizes this information in various ways, such as described in U.S. patent application Ser. No. 11/510,106, filed Aug. 25, 2006, entitled System And Method For Improved Low Flow Medical Pump Delivery, which is hereby incorporated by reference herein. One way includes associating the incoming force/pressure data with a particular travel value within the pumping cycle, such as a time, a linear distance, and/or rotational distance or angle of travel. One of ordinary skill in the art will appreciate that the position sensor 48 could alternatively track a cam attached to the shaft 42 or the pumping element 44. Additionally, one of ordinary skill in the art will appreciate that the position sensor 48 as used herein includes but is not limited to mechanical indicators such as pivoting dial indicators, electronic switches, Hall Effect sensors, and optical based position detectors.

In a preferred embodiment, the motor 38 is a brush DC motor with a 128 count magneto-resistive encoder that is used in quadrature, for a total resolution of 512 counts per motor revolution. Depending on the number of motor shaft 42 rotations needed to perform a pump cycle, the cycle can be divided into a very fine number of positions. For example, if it takes 10 rotations of the pump shaft 42 to complete one pumping cycle or stroke (360 degrees in one embodiment), each cycle can be separated into 5120 travel positions or values. Thus, in this example, the position sensor 48 can provide information which allows for a resolution of 5120 travel positions per cycle for the processing unit 30 to determine and/or utilize within other calculations and determinations.

One or more air sensors or air detection sensors 60 are operatively associated with the processing unit 30 for detecting air in the fluid line, such as in the outlet fluid line 22. The processing unit 30 receives signals and/or data from the air detection sensor(s) 60. In one embodiment of the medical pump 10, the air detection sensor(s) 60 is pressed against and is in physical contact with the exterior surface of the outlet fluid line 22 tubing. The power supply can provide power to the air detection sensor(s) 60 (connection lines not shown), which is configured to excite the outlet fluid line 22 with ultrasonic waves to generate and provide an analog signal to the processor. The analog signal from the air detection sensor(s) 60 is converted to digital data, providing accurate air content data of air contained within the outlet fluid line 22, as will be explained in greater detail below. In normal operation, in general, this air content data falls within an expected range, and the processing unit 30 (and therein, as understood to a person of ordinary skill) determine that proper fluid flow is in progress. When the air content data falls outside the expected range, in general, the processing unit 30 determines and indicates that improper air content is being delivered to the patient. As is explained in greater detail herein, the processing unit 30 can control the air detection sensor(s) 60 and make various determinations to more accurately detect whether improper air is within the fluid delivery line, such as within the outlet fluid line 22.

Figure 2:
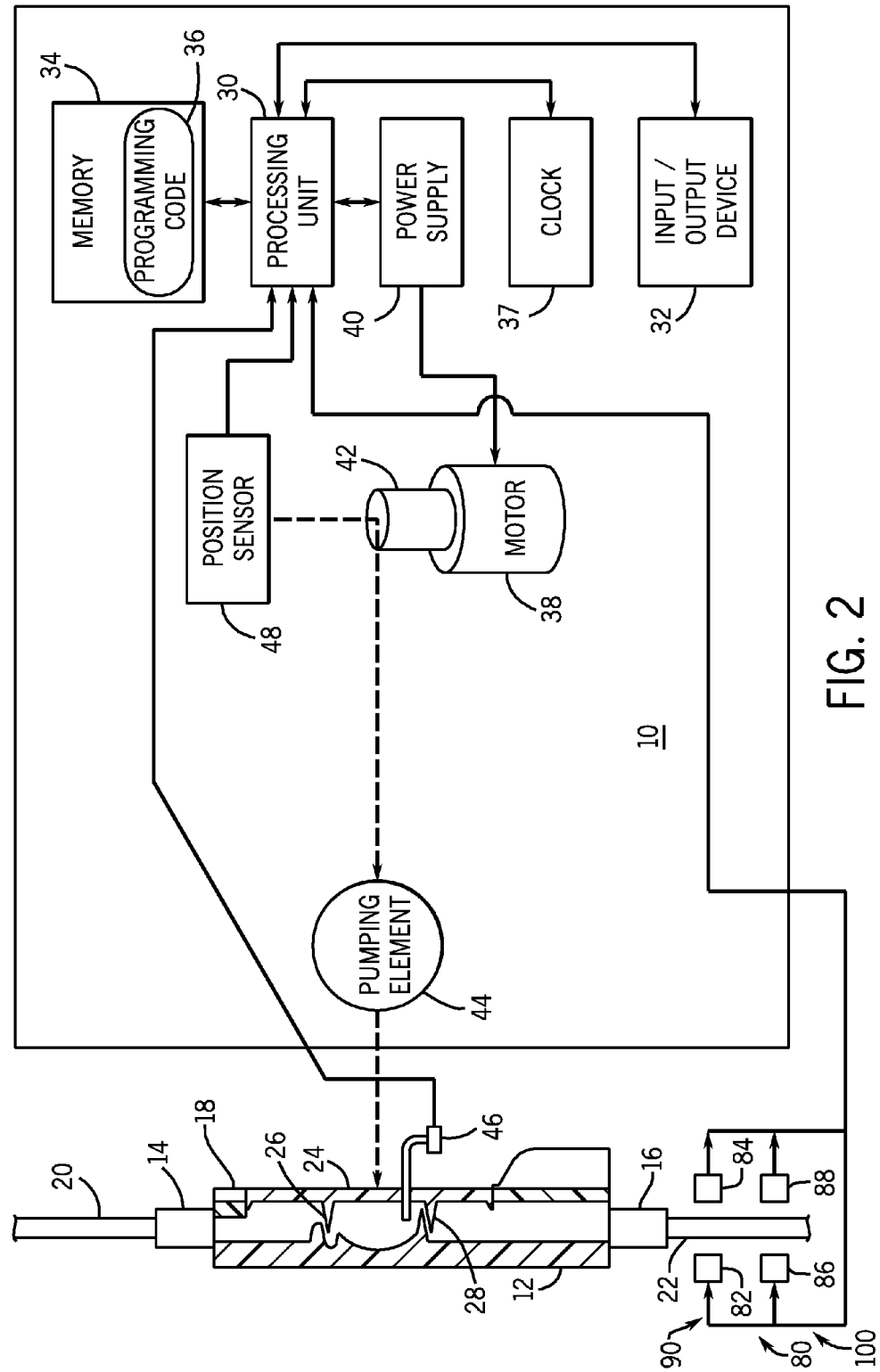
FIG. 2 is an illustration of another embodiment of a medical pump of the present invention, wherein multiple air sensors are provided.

FIG. 2 depicts an embodiment similar to that shown in FIG. 1. However, a specific cassette 12 is depicted with the internal construction shown. In addition, a dual air detection sensor arrangement 80 is shown.

Specifically, as shown in FIG. 1, the cassette 12 may include an inlet 14 and an outlet 16 formed in main body 18. An inlet fluid line 20 couples the inlet port 14 on the main body 18 to a fluid source such as an IV bag or other fluid container. Similarly, an outlet fluid line 22 couples the outlet port 16 on main body 18 to the body of a patient. As shown in FIG. 2, an inlet valve 26 and outlet valve 28 are located within the main body 18. The pumping chamber 24 is connected in fluid flow communication between the inlet port 14 and the outlet port 16. The pumping chamber 24 operates to meter fluid through the cassette 12. The inlet valve 26 resides between inlet port 14 and the pumping chamber 24. Inlet valve 26 operates to physically open and close the fluid communication between inlet port 14 and pumping chamber 24. The outlet valve 28 resides between the pumping chamber 24 and outlet port 16. Outlet valve 28 operates to physically open and close the fluid communication between pumping chamber 24 and outlet port 16. The pumping chamber 24, inlet valve 26, and outlet valve 28 are all operatively associated with the pump 10 to control the flow of fluid through the cassette 12. The cassette is a passive valve system requiring pressurization of the pumping chamber 24 prior to fluid delivery. Inlet valve 26 and outlet valve 28 react to the pressure of the pumping element 44 on the pumping chamber 24. In operation, a substance such as a fluid enters through the inlet 14 and is forced through outlet 16 under pressure. The fluid is delivered to the outlet 16 when the pump 10 compresses the pumping chamber 24 to expel the fluid. Additional details of this cassette and other details and information may be found in U.S. Patent Application Publication No. 2005/0214129 A1, published Sep. 29, 2005, the entirety of which is hereby incorporated by reference herein and made a part of this specification.

In the embodiment of FIG. 2, the force/pressure sensor 46 comprises a pressure probe located at least partially within the pumping chamber 24 of the cassette 12. The current signal from pressure probe is proportional to the force exerted on the pumping chamber 24 by the pumping element 44. As is also the case in FIG. 1, the force/pressure sensor 46 is the only force/pressure sensor included in the medical pump 10, and operates to sense the force/pressure on pumping element 44 as well as to generate a force/pressure signal to the processing unit 30 based on this force/pressure. One skilled in the art will appreciate that the present invention is applicable regardless of the type and location of the force/pressure sensor.

The medical pump 10 of the present invention provides a mechanism for controlling or adjusting an actual delivery of fluid based on variations from nominal data used to estimate pump performance. The processing unit 30 retrieves the operating condition programming code 36 from memory 34 and applies it to the force/pressure and travel data received during a pump cycle. The force/pressure data and travel data are processed by the processing unit 30. Sensing the force/pressure, for example, that the pumping chamber 24 exerts against the pumping element 44, and analyzing that force/pressure data can determine various parameters for use in the operating the medical pump. The processing unit 30 utilizes these parameters in a closed loop cycle/stroke feedback system to determine and/or calculate delivery parameters. Additional information about this and other embodiments of the medical pump 10 can be found within U.S. patent application Ser. No. 11/510,106, filed Aug. 25, 2006, entitled System And Method For Improved Low Flow Medical Pump Delivery, which is hereby incorporated by reference herein.

In addition, as shown in FIG. 2, a multiple air detection sensor assembly 80 is provided. In one embodiment the multiple air detection sensor assembly 80 is a dual air detection sensor assembly. The dual air detection sensor assembly 80 includes a first air detection sensor 90 and a second air detection sensor 100. The first air detection sensor 90 includes a first transmitter 82 and a first receiver 84. The second air detection sensor 100 includes a second transmitter 86 and a second receiver 88. The first and second transmitters 82, 86 are positioned within the medical pump 10 at a location which is adjacent to a first side of the fluid delivery line 22 when the fluid delivery line 22 has been installed or mounted by a caregiver within the medical pump 10. The first and second receivers 84, 88 are positioned within the medical pump 10 at a location which is adjacent to a second and opposite side of the fluid delivery line 22 to the first side when the fluid delivery line 22 has been installed or mounted by a caregiver within the medical pump 10.

The first and second transmitters 82, 86 each transmit ultrasonic signals which travel through the fluid delivery line 22, and which are received by the respective first and second receivers 84, 88 on the opposite side of the fluid delivery line 22 from the first and second transmitters 84, 88. Each signal transmitted by the first and second transmitters 82, 86 and received by the respective first and second receivers 84, 88 is modified or affected by the physical elements (the fluid delivery line, air within the fluid delivery line, fluid within the fluid delivery line, etc.) the signal encounters between the respective pairs of first and second transmitters 82, 86 and receivers 84, 88. The control of the first and second air detection sensors 90, 100 as well as the use of the signals generated by these sensors will be described in greater detail below with reference to FIGS. 4-6, as well as other figures.

With continued reference to FIGS. 1 and 2, the memory 34 with the processing unit 30 and stores program code 36 and data necessary for the processing unit 30 to calculate and output the operating conditions of medical pump 10. The processing unit 30 retrieves the program code 36 from memory 30 and applies it to the data received from various sensors and devices of the medical pump 10. Specifically, the processing unit 30 processes the data from the medical pump 10 to determine various operating conditions, including when there is proper flow of fluid through the cassette 12 to the patient, and if air bubbles are in the fluid delivery line, such as air bubbles entrained in the fluid leaving the cassette 12. Once the operating condition has been determined, the processing unit 30 can output the operating condition to the display 32, activate the indicator or alarm, and/or use the determined operating condition to adjust operation of the medical pump 10.

Once the cassette 12 is fully seated correctly and pumping operation begins, the array of pressure data is analyzed by the processing unit 30 to determine proper flow of fluid through the cassette 12 to the patient. In one use, the processing unit 30 uses this pressure signal from pressure sensor 46 to determine that the cassette is properly pressing on the pumping element 44 and activates the pumping element 44 to begin pumping the cassette 12. Similarly, the processing unit 30 determines the orientation and presence of cassette 12 by processing data received from an orientation sensor (not shown). Where the cassette 12 is incorrectly oriented (backwards or upside down, for instance), where there is no cassette at all, or where the cassette 12 is not fully seated, the processing unit 30 determines that improper proper cassette loading has occurred.

Additionally, once the processing unit 30 processes data received from the orientation sensor to determine the presence of a properly loaded cassette in an open carriage assembly, the processing unit 30 can be programmed to automatically close the carriage assembly after a given period of time and without a direct user command. This can be performed manually as well. The processing unit 30 communicates with the display/input device 32 and allows the user to receive output from processing unit 30 and/or input (data or commands) into the processing unit 30. When the cassette 12 is loaded into the open carriage assembly, a user accesses the display/input device 32 to command the medical pump 10 to automatically close the carriage assembly. Likewise, a user accesses the display/input device 32 to command the medical pump 10 to automatically open the carriage assembly when the cassette 12 is to be removed and/or replaced.

Figure 3:
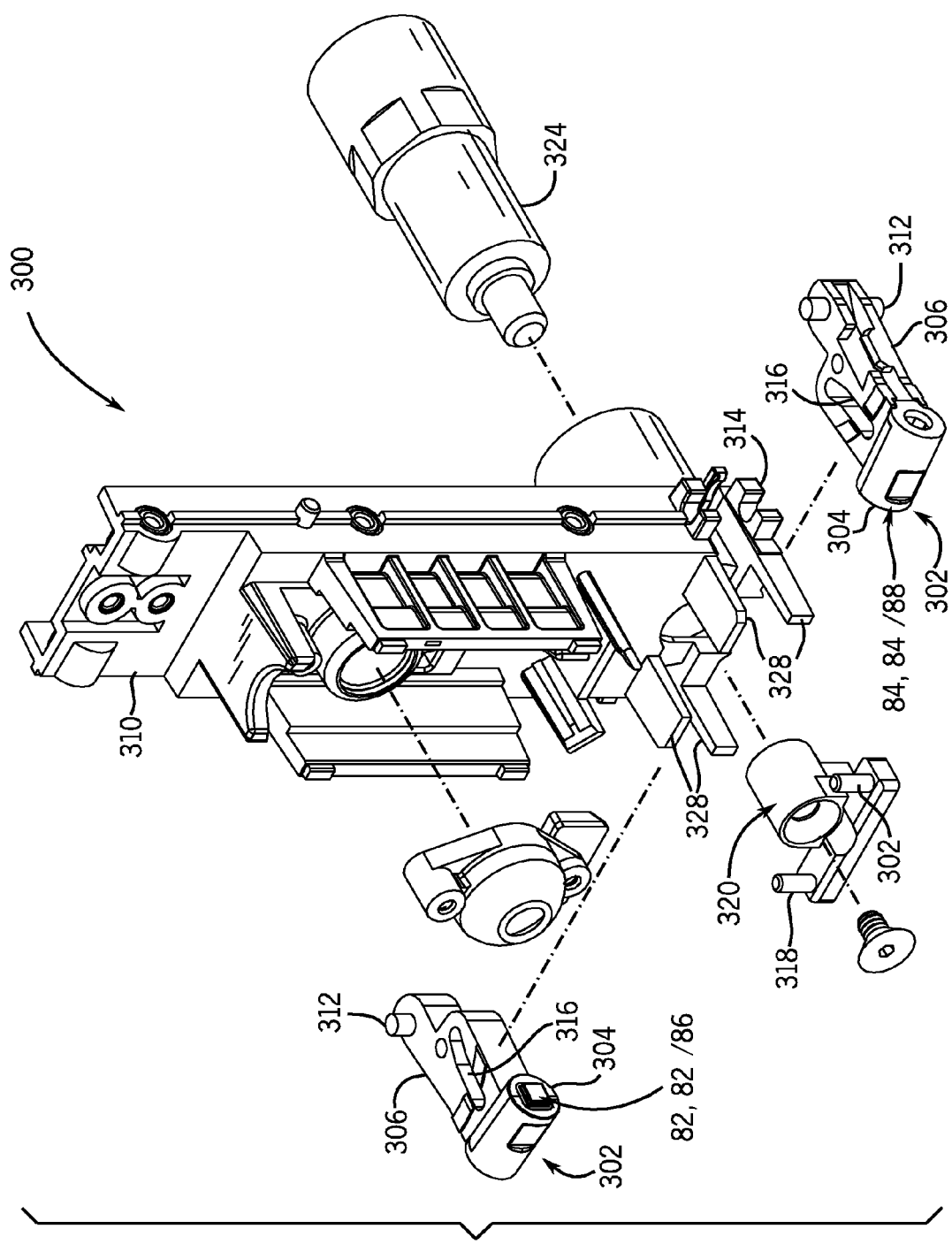
FIG. 3 is an exploded view of one embodiment of an air detection sensor and cassette receiver assembly of a medical pump of the present invention.

Referring to FIG. 3, an exploded assembly view illustrates the functional components of one carriage assembly 300, including one embodiment of an air detection sensor assembly. Specifically, a pair of air detection sensor carriers 302 including sensor heads 304 attached to the near ends of air sensor arms 306. In one embodiment of the carriage assembly 300 of FIG. 3, one of the air detection sensor heads 304 is a first transmitter 82 and one of the air detection sensor heads 304 is a first receiver 84, which together define an air sensor 60 as described above in relation to FIG. 1. In another embodiment of the carriage assembly 300 of FIG. 3, one of the air detection sensor heads 304 includes/mounts the first transmitter 82 and a second transmitter 86 spaced from the first transmitter 82 along the length of the outlet fluid line 22 (here axially or vertically) and one of the air detection sensor heads 304 includes/mounts the first receiver 84 and a second receiver 88 similarly spaced from the first receiver 84 along the length of the outlet fluid line 22 to define a multiple air detection sensor arrangement 80, as shown in FIG. 2 and referred to above. The arms 306 are pivotally secured to the base surface 310 at hinges, which each comprise a pin member 312 and a socket 314 for pivotally receiving the pin member 312. The arms 306 each have a cam slot 316 formed therein that receive cam posts 318 located on air sensor cam 320. An air sensor actuator 324 is associated with the air sensor cam 320 to open and close the air sensor arms 306. Guide elements 328 extend from the base surface 310 to guide the movement of both the arms 306 and the air sensor cam 320. While FIG. 3 shows a single pair of air detection carriers 302 for mounting the multiple sensor arrangement 80, one skilled in the art can appreciate that multiple spaced air detection sensor carriers 302 can be provided on the arms 306. Alternatively, multiple arms 306, each with a single air detection sensor carrier 302 can be used to mount a multiple sensor arrangement.

When the carriage assembly 300 is traveling to an open position, the processing unit 30 (not shown) activates the air sensor actuator 324 (via power supply 40, not shown) to force the air sensor cam 320 inward, pivoting the arms 306 about the hinges and moving the sensor heads 304 apart. When the carriage assembly 300 is traveling to a closed position, the processing unit 30 (not shown) activates the air sensor actuator 326 to force the air sensor cam 320 to move outward, pivoting the arms 306 about the hinges and moving the sensor heads 304 together. The cam slots 316 can be designed to include a rapid travel zone where the cam slot 316 profile is such that the arms 306 close rapidly until the transmitter/receiver pairs 82/84 (and 86/88, where applicable) touch the fluid delivery line 22 (not shown). The cam slots 316 can also have a compression zone where the cam slot 316 profile is such that the arms 306 are gradually compressed, as well as a "dwell" zone where each cam slot 316 profile is straight and the arms 306 do not close further with additional movement of air sensor cam 320. It will be appreciated that the air sensing aspects of the present invention are applicable to other types of medical pumps, including but not limited to syringe pumps, reciprocating plunger pumps and peristaltic pumps. For example, the carriage loader can automatically load a syringe or section of tubing and the air detection sensors 60, 90, 100 on carriers 302 can sense air present in the syringe, tubing connected thereto, or a section of tubing not associated with a syringe.

Figure 4:
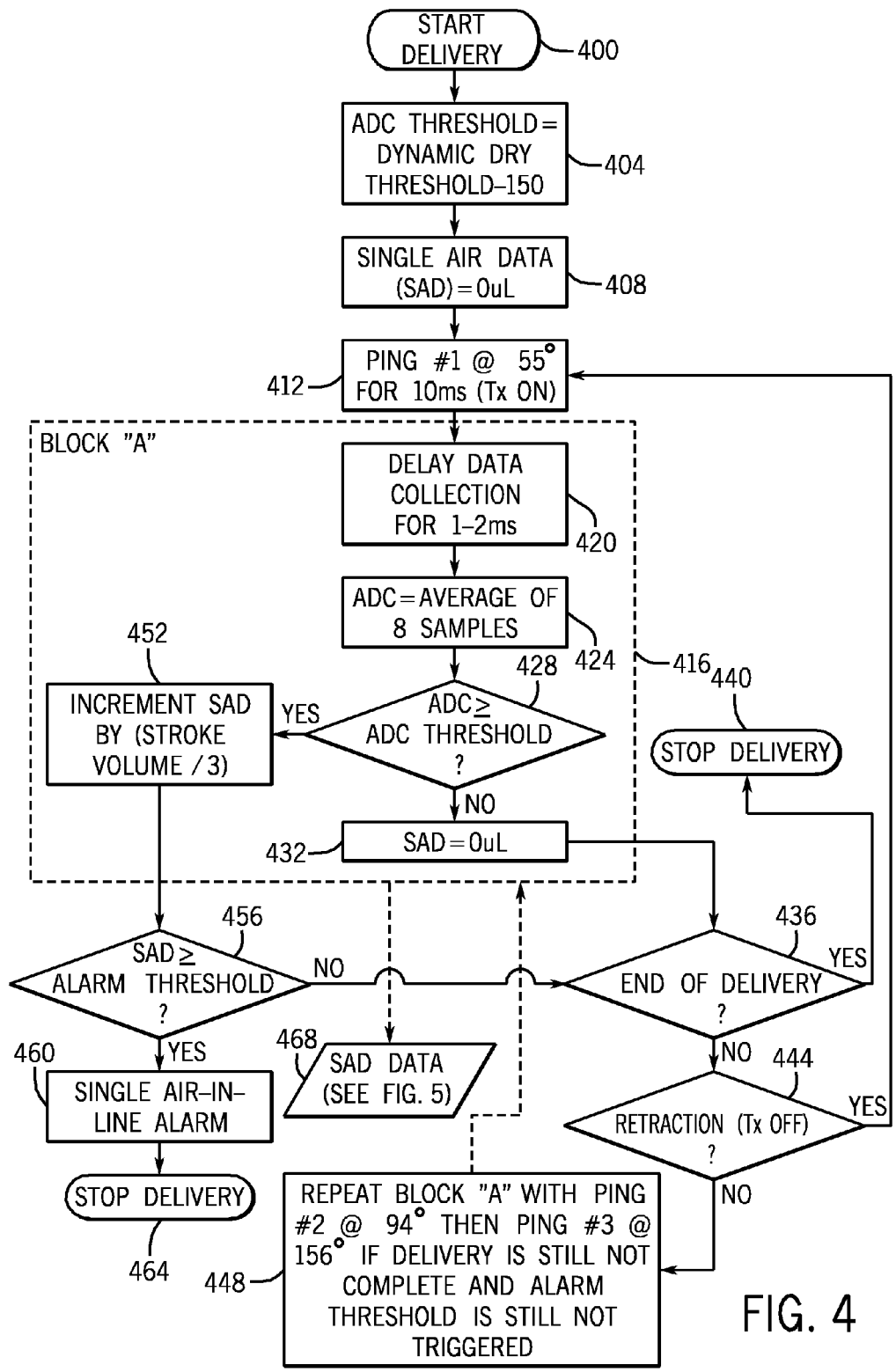
FIG. 4 is a flow chart of one method of operating one embodiment of the medical pump of the present invention, wherein single air in line detection is provided.
Figure 5:
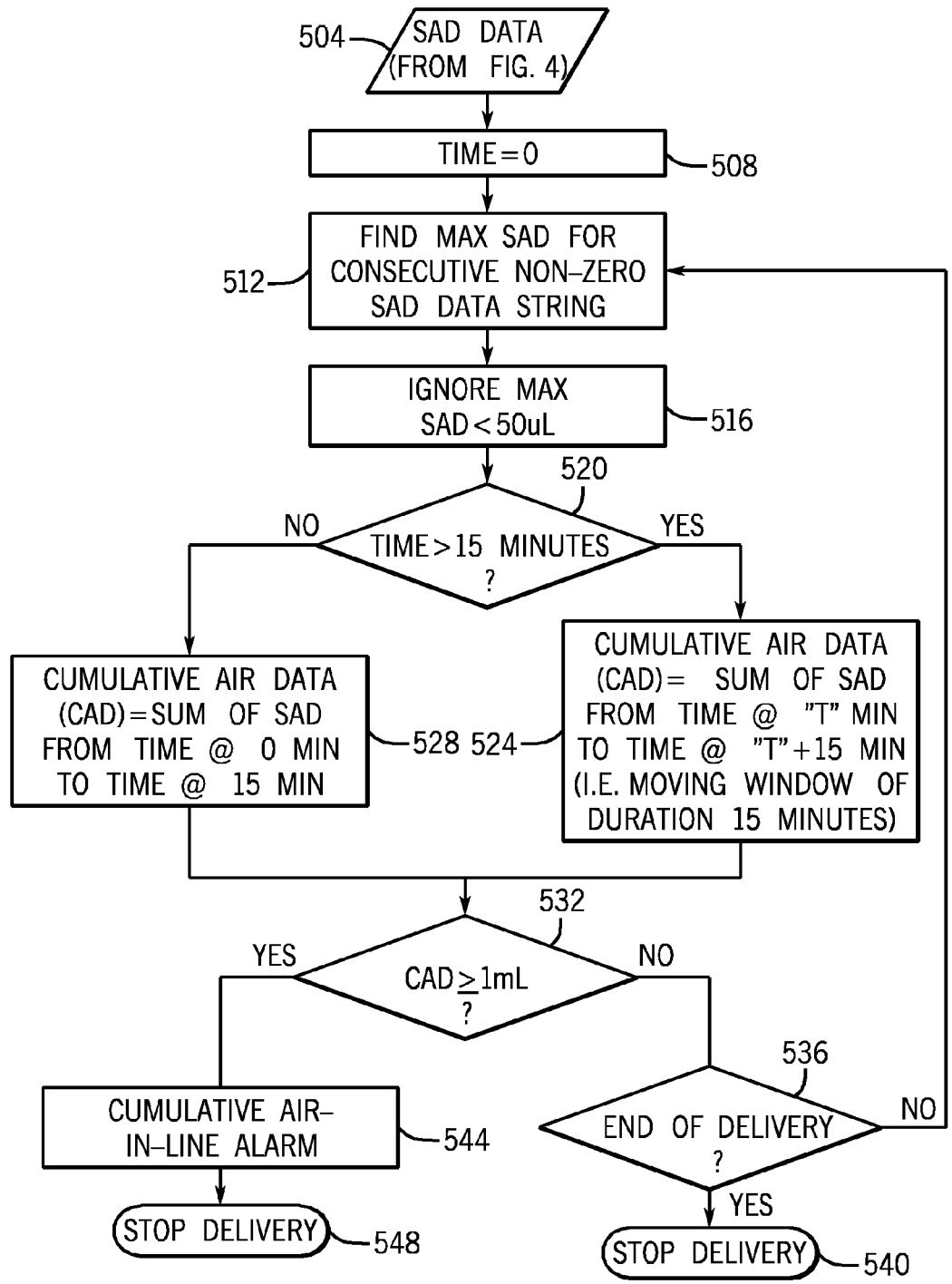
FIG. 5 is a flow chart of one method of operating another embodiment of the medical pump of the present invention, wherein cumulative air in line detection is provided.
Figure 6:
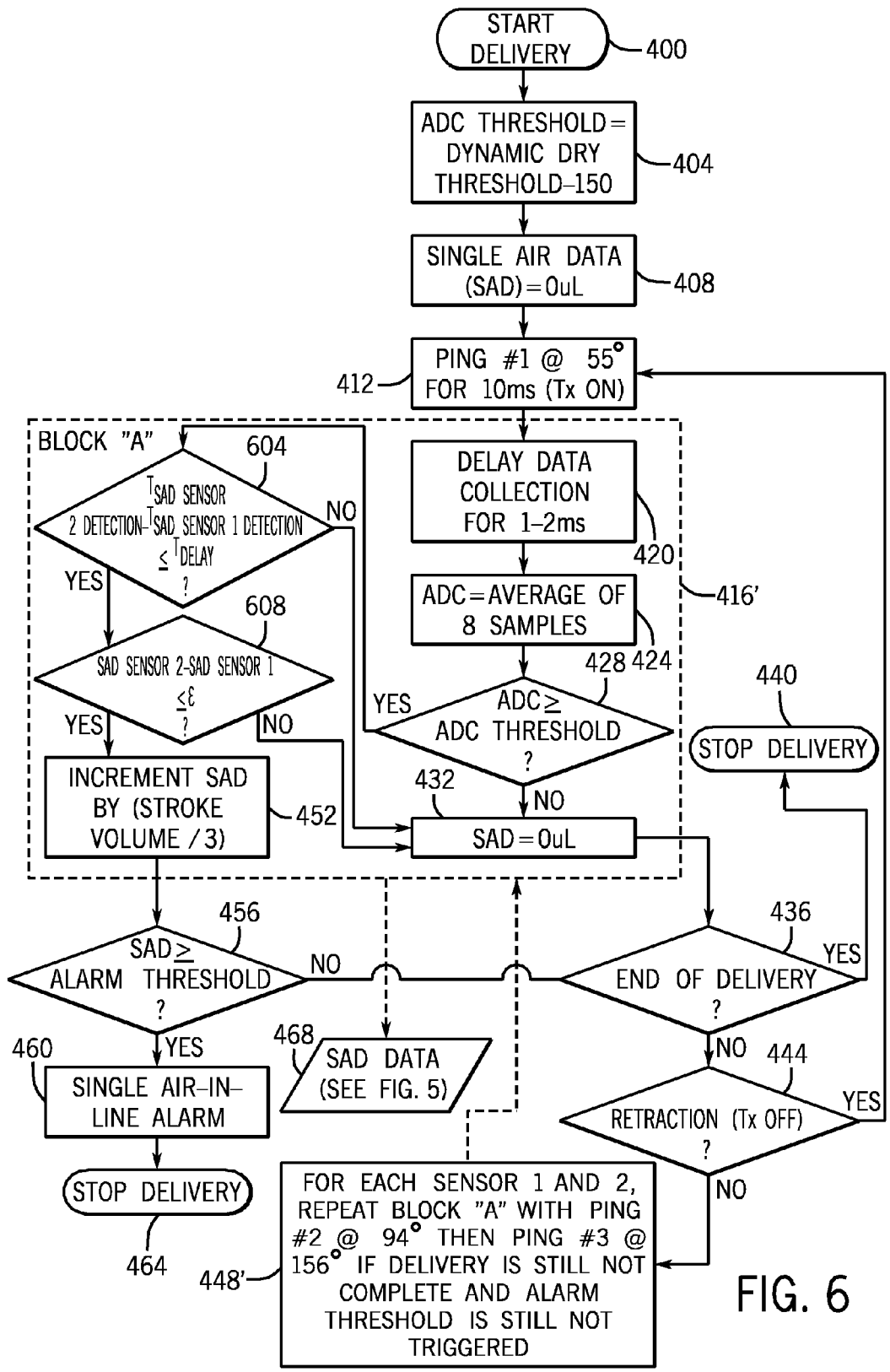
FIG. 6 is a flow chart of one method of operating a medical pump according to the present invention, wherein single air in line detection is provided for one multiple air sensor embodiment.

With reference to FIGS. 4-6, the operation of the air detection sensors 60, 90, and 100 will now be described in conjunction with the processing unit 30 and the programming code 34 running therein, for detecting air in the fluid delivery line. The following description assumes that the cassette 12 has already been inserted and installed into the carriage assembly 300. To carry out detection of the air in the fluid delivery line, in one embodiment, the processing unit 30 executes the programming code 36. Referring to FIGS. 4 and 5, the general execution of one embodiment of the programming code 36 is shown for an air detection assembly 80 having one or a first air detection sensor 60, 90 (shown in FIGS. 1 and 2). Reference is made to a second air detection sensor 100 and respective components thereof, from time to time, when applicable to the second air detection sensor 100, for ease of understanding a later-described multiple air detection sensor embodiment, such as for example a "dual air sensor" embodiment shown in FIG. 6.

FIG. 4 shows a single air in line detection flow diagram. Specifically, block 400 represents the beginning of the method, which includes the pump drive, such as the motor 38 and/or the pumping element 44, in a cycle start position. Most of the remaining blocks represent operations of the programming code 36 which execute each time the processing unit 30 loops through the programming code 36, until interrupted or a branch in the programming code 36 causes an action to occur. For ease of presentation, many intermediary steps and programming loops are not shown, many of which are either known to one of ordinary skill in the art and/or are incorporated by reference herein from another specification.

Continuing, block 404 represents an operation of setting a first predetermined air threshold, either at set up time of medical pump 10 or some time prior to fluid being introduced into the fluid delivery line 22. Specifically, the processing unit 30 receives an analog signal from the first receiver 84 of the first air detection sensor 90 when the processing unit 30 knows that there is no fluid in the fluid delivery line 22. This analog value is converted to a digital value represented by "ADC" (Analog to Digital Converted value) in FIGS. 4-6. As an aside, in one embodiment, each ADC value is an average of a plurality of samples taken proximate in time, to reduce errors in reading the analog values, such as taking eight (8) samples and averaging the samples to obtain an ADC value. Further, the analog value, which is a voltage, is converted to a digital value within a digital range of 0 to 4095, for enhanced accuracy and ease of processing. This range is provided for determining the difference between air and fluid within the fluid delivery line 22. In one embodiment, twelve bits of digital data are provided by the air detection sensor 90, 100 for use by the processing unit 30, as described herein.

Continuing with block 404, to obtain the first predetermined threshold, an offset value, such as one hundred and fifty (150), is subtracted from the ADC value measured while no fluid is in the fluid delivery line 22, to reduce "false air" indications. The processing unit 30 can initiate and perform this calibration using a benchmark, as follows: the air detection sensors 90, 100 return an $ADC_{dry}$>3350 with the transmitter(s) 82, 86 turned off (dry measurement), even though there may still be a fully primed macro bore tube within the air sensor (between the transmitter(s) 82, 86 and receiver(s) 84, 88. The processing unit 30 then performs the same determination with the transmitter(s) 82, 86 turned on (wet measurement "$ADC_{wet}$"). The air detection sensor(s) return values which should comply with $ADC_{wet}$<$ADC_{dry}$−400. This preferred offset of four hundred (400) was empirically determined. Specifically, the selection of the ADC values (what constitutes mostly fluid or what constitutes mostly air based on detection criteria) is based on averaging hundreds of test data for different fluids, tube types, at different temperatures. Using a single threshold is done so that one technology solution can work across different scenarios (i.e. this works at a 90% or greater confidence level), without the added expense of implementing a dynamically established threshold. In doing so, the robustness of the system may be reduced slightly and a higher margin of error may exist. One way to remedy this would be to dynamically select or determine unique (varying) thresholds for each type of tubing, temperature and/or medication (fluid) used. The information needed by the processor to make this determination can be provided within a bar-code on a medication vial, delivery set (bag and tubing set). A drug (fluid)/tubing/temperature library could be stored within the pump, and/or stored and/or downloaded from a central server. The library could be built having an appropriate set of threshold for each tube type, fluid type, and/or temperature. This determination could also be performed by dynamically detecting or measuring the force/torque required to close in on the tube for the motor used to operate the air sensor arms. The pump could include a thermal sensor to measure and create temperature information. These parameters would allow unique and/or shift-on-the-fly adjustment/dynamic generation of the thresholds, and would likely establish an even greater robustness, nearing or meeting a 100% confidence level.

During operation of the medical pump 10, the process utilizes certain predetermined or dynamic values. Specifically, the dynamic threshold of first predetermined threshold is the value with the transmitter disabled just prior to delivery. The first predetermined threshold is stored in the memory 34 for later use. This value can alternatively be obtained or set just after calibration of the medical pump 10 occurs, before fluid is provided into the fluid delivery line 22. Typical ADC values that might indicate air in the fluid delivery line 22 are between 3200 and up (theoretical max is 4095). Typical ADC values that might indicate fluid in the fluid delivery line 22 are between 500 to 3200. In general, low ADC values indicate a higher volume or percentage of liquid and high ADC values indicate a higher volume or percentage of air in the fluid delivery line 22 adjacent the air detection sensor(s) 90, 100.

At block 408, the processing unit initializes an air in line counter, referred to as "Single Air Data" or "SAD" in the embodiment shown in FIG. 4, by setting the air in line counter to zero. Block 408 takes place prior to determining if there is any air in the fluid delivery line 22 or the taking of any "live" air detection sensor 90, 100 measurements or readings. Prior to taking any measurements, no power is provided to the first and second transmitter(s) 82, 86, and therefore, no ultrasonic signal is transmitted by the first and second transmitters 82, 86 at the start of the delivery. It has been found that providing a continuous transmission of an ultrasonic signal from the first and second transmitters 82, 86 through the fluid delivery line 22 can enhance air bubble creation and/or break up air larger bubbles into smaller air bubbles, thereby aggravating air bubbles in the fluid delivery line 22, and making the detection of air bubbles more difficult. Thus, referring to block 412, the processing unit 30, and programming code 36 therein, continuously receives position information from the position sensor 48 and determines an amount of time and/or distance that the pumping element 44 has traveled since the beginning of the pumping cycle. As mentioned, each pumping or fluid delivery cycle or "stroke" includes a pressurization phase, a pumping phase, and a retraction phase, in the context of the embodiments of FIGS. 1 and 2.

The following provides a brief explanation of the pressurization phase, pumping phase, and retraction phase, and one embodiment to determine and track these phases, for a better understanding of the present embodiment. At the beginning of a pumping cycle, the pump drive 42 causes the pumping element 44 to advance toward and eventually apply a force/pressure on the pumping chamber 24 (see FIGS. 1 and 2). The cycle or pump drive start position has a pump drive position value and/or a time value associated therewith, which is stored in the memory 34 by the processing unit 30 at the start of the cycle. The cycle begins at 0 degrees, or Bottom Dead Center (BDC) in a cam embodiment, with the pumping element 44 applying a force/pressure to the pumping chamber 24 a minimal amount at this point. The start position of the pump drive, such as the pumping element 44, is at 0 degrees. This begins the pressurization phase of the cycle. Empirical data has shown that the true end of the pressurization phase ranges from about 0 degrees to about 30 degrees. However, determining the actual end of the pressurization phase and the beginning of delivery phase can be difficult, and is one of the subjects of U.S. patent application Ser. No. 11/510,106, filed Aug. 25, 2006, entitled System And Method For Improved Low Flow Medical Pump Delivery. During the pressurization phase of the cycle, the pumping element 44 moves into the cassette 12 (which may be referred to as the pressurization stroke because fluid is compressed in pumping chamber 24 of the cassette 12 in one embodiment) building force/pressure within the pumping chamber 24, while the outlet valve 28 remains closed. In one embodiment, the force/pressure provided by the pressure sensor 46 is tracked and various calculations can be used to determine when the pressurization phase has ended and when the delivery phase has begun. In general, when the outlet valve 28 shown in FIG. 2 has opened, the delivery phase of the pumping cycle begins.

When the processing unit 30 makes the determination that the delivery phase has begun, the processing unit 30 also determines and stores the time and the linear and/or angular position of the motor 38 and/or the pumping element 44 in memory 34 for reference purposes, one or more of which will be used in subsequent determinations by the processing unit 30. In one embodiment, the effective delivery cycle or delivery phase of the pumping cycle is generally from about 30 degrees to 180 degrees of the rotation. However, since the processing unit 30 has determined when the end of the pressurization phase has occurred and the processing unit 30 receives sensed position information of where the pump drive is positioned, such as the rotary or stepper motor position information, the processor can determine how much additional travel is needed to complete the delivery phase of the pump cycle and utilizes this remaining travel value to accurately control the delivery phase.

Once the processing unit 30 has made the necessary delivery parameter determinations, the processing unit 30 controls the driving of the pump drive, such as stepping of the pump motor 38, utilizing determined parameters. When the processing unit 30 determines that the delivery phase is complete, the processing unit 30 sends a signal to stop the pump drive from continuously driving the pump drive. When the effective delivery cycle is complete, the processing unit 30 causes the pump drive to be reset to the beginning of the next cycle. For example, in one embodiment using a cam, the pump drive is driven for a predetermined or calculated time to bring the pump drive to the beginning of the next cycle. In particular, the effective delivery phase of the pump cycle ends at 5 degrees short of Top Dead Center (TDC), or 175 degrees of rotation, and a retraction or depressurization phase begins at 180 degrees. The depressurization phase depressurizes the pumping chamber 24, which occurs from about 180 to 210 degrees. During the depressurization phase, the pumping element 44 moves out of the cassette 12 (which is called the up-stroke, depressurization or inlet stroke) and the force/pressure drops off. As the pumping element returns to its initial position, while the inlet valve 26 remains closed, negative pressure builds within the pumping chamber 24. A refill phase within the retraction phase begins when the negative pressure within the pumping chamber 24 is sufficient to the open the inlet valve 26. During the refill phase, the pumping element 44 moves out of the cassette 12 building negative pressure within the pumping chamber 24 sufficient to open the inlet valve 26 and draw fluids into the pumping chamber 24. The refill phase of the retraction phase occurs from about 210 to 360 degrees, or Bottom Dead Center (BDC), which brings the pump drive to the beginning of the next cycle.

Continuing with the embodiments shown in FIGS. 4-6, in the context of the above-described three-phase delivery cycle, the processing unit 30 does not provide any power to the transmitter(s) 82, 86 and/or provides a signal to the transmitter(s) 82, 86, preventing the transmitter(s) 82, 86 from emitting any ultrasonic signals necessary for the detection of air in the fluid delivery line 22, during the pressurization phase and during the retraction phase. Further, the processing unit 30 does not provide any power to the transmitter(s) 82, 86 and/or provides a signal to the transmitter(s) 82, 86, preventing the transmitter(s) 82, 86 from emitting any ultrasonic signals necessary for the detection of air in the fluid delivery line 22, at the beginning of the delivery phase. After a first predetermined cycle parameter value has been met, the processing unit 30 activates or causes power to be provided to the first transmitter 82 of the first air detection sensor 90, and in a dual air sensor embodiment, to the second transmitter 86 of the second air detection sensor 100. This and other predetermined cycle parameter values can be an amount of time that has passed after the stroke cycle has begun, can be an angular distance that the pump drive has traveled, can be a linear distance that the pumping chamber has moved, and/or some other time, distance or other parameter which spaces the activation of the sensor from the beginning of the stoke cycle or from some other reference point. In the embodiment shown in FIG. 4, block 412 shows that the processing unit 30 is causing "Ping #1" to occur at or after fifty-five (55) degrees of rotation of the pump drive 38, 42 from the beginning of the pumping cycle. "Ping #1" represents the processing unit 30 causing the first transmitter 82 to transmit ultrasonic signals and the first receiver 84 receiving such ultrasonic signals. Thus, the medical pump 10 measures a first air content signal generated by the first air detection sensor 90. In the embodiments shown in FIGS. 4-6, the ping or ultrasonic signal transmission lasts for ten (10) milliseconds (ms) and eight samples are taken by the processing unit 30 during the ping. After the ping is completed, the transmitter(s) 82, 86 return to their previous deactivated operating state, with the processing unit 30 not providing any power to the transmitter(s) 82, 86 and/or providing a signal to the transmitter(s) 82, 86, preventing the transmitter(s) 82, 86 from emitting any ultrasonic signals necessary for the detection of air in the fluid delivery line 22. In the three-phase delivery cycle embodiment of the present invention, at least a plurality of "pings" will be provided and spaced apart in an attempt to minimize bubble creation and dancing bubbles, yet at the same time detect bubbles in the optimal manner. Thus, determining how many and where to place the "pings" is significant. In one embodiment, the following steps can be taken to optimize the location of (when) the first ping occurs. Based on at least the disclosure within U.S. patent application Ser. No. 11/510,106, filed Aug. 25, 2006, entitled System And Method For Improved Low Flow Medical Pump Delivery, a skilled artisan would know how to detect the end of the pressurization phase of delivery using a force sensor, as provided therein. Thus, when the outlet valve of the cassette "cracks," and the actual fluid delivery begins (end of pressurization angle/beginning of the fluid delivery phase), the angle of shaft rotation or time at which this occurs can be used to locate the beginning of the first "ping," using an offset value (delay in angle or time) from the beginning of the delivery phase. The location of another "ping" or other "pings" can also be based on the determination of the beginning of the delivery phase, by a further offset value from the beginning of the delivery phase, from the beginning/end of the prior "ping," or some other reference point. With reference to pump embodiments described herein and within the above-referenced patent application, the last "ping" within the delivery phase of pumping cycle should end at or before 175 degrees of shaft rotation, since toward the end of the delivery phase, not much fluid is delivered (thus, there is not much fluid movement). This approach can also be used in non-low flow embodiments and in other embodiments, such as at least the other embodiments disclosed in the above referenced patent application.

The samples of the air content signal are at least briefly stored in the memory 34 and the processing unit 30 averages the samples of the air content signal to obtain a more reliable measurement. As will be explained further below, in one embodiment, additional pings are provided during the delivery phase. Specifically, one potential commercial embodiment includes additional pings at ninety-four (94) degrees ("Ping #2") and at one hundred fifty-six (156) degrees ("Ping #3") of rotation of the pump drive 38, 42 from the beginning of the pumping cycle. The pings can also be measured relative the beginning of the delivery phase (calculated or otherwise), or some other reference point. Block "A" or 416 represents a portion of the programming code 36 which is performed for each ping of the air detection sensor(s) 90, 100, such as the ping at fifty-five (55) degrees in FIG. 4. Block A includes block 420 and block 424. Block 420 represents a predetermined delay time which the processing unit 30 lets pass before collecting the samples of the air detection signals received by the processing unit 30 from the first air detection sensor 90, and from the second air detection sensor 100 in the dual air sensor embodiment described below. The processing unit 30, the air detection sensors 90, 100, or some other hardware device can generate air content data from the air content signal. The analog signal is converted to a digital value or data representative of the signal measured by the air detection sensor(s) 90, 100. As mentioned, the processing unit 30 can receive a plurality of samples for each of the air content signals, convert each of the samples from an analog signal to a digital value, store the digital values and then average the stored values. Alternatively, the processing unit 30 may receive already converted values as air content data, in digital form, and then store and average the digital samples. The average of the digital samples can also be considered as air content data. FIG. 4 refers to this averaged air content data as "ADC". The flow then moves to block 424, which represents the averaging of the digital samples to obtain "ADC".

The flow then moves to block 428, which is also a part of block A. Block 428 represents the processing unit 30 determining whether the air content data (or air detection data) has met a first predetermined air threshold. At block 428 in the embodiment shown in FIG. 4, the processing unit 30 determines whether "ADC" is greater than or equal to the ADC threshold as previously determined or set at block 404. In one embodiment, the first predetermined air threshold being met represents that there is air in the fluid delivery line. If this determination is not true, the flow moves to block 432. At block 432, the air in line counter or "SAD" (Single Air Data) is set to zero. From block 432, the flow then moves to block 436, which represents the processing unit 30 determining whether the medical pump 10 is at the end of the fluid delivery, typically occurring when a predetermined about of fluid has been delivered or provided by the medical pump 10 to a patient. If the fluid delivery is complete, the flow moves to block 440 and the processing unit 30 stops the delivery and the stops operation of the medical pump 10. If the fluid delivery is not complete at block 436, the flow then moves to block 444, which represents the processing unit 30 determining whether the delivery phase of the pumping cycle is complete and whether the retraction phase of the pumping cycle has been reached. If the determination at block 444 is true, the flow then moves back to block 412, for providing the next ping at the appropriate time/travel distance within the delivery phase of the next pumping cycle. If the determination at block 444 is not true, the flow then moves to block 448, which represents the medical pump 10 providing a "ping #2" and a "ping #3". In one embodiment, "ping #2" is at ninety-four degrees and "ping #3" is at one hundred fifty-six degrees of rotation of the pump drive 38, 42 from the beginning of the pumping cycle. "Ping #2" and "ping #3" each represent the processing unit 30 causing the transmitter 82, 86 to transmit ultrasonic signals and the receiver 84, 88 receiving such ultrasonic signals. Similar to "ping #1", in one embodiment the ping or ultrasonic signal transmission by the transmitter lasts for ten (10) milliseconds (ms) and eight samples are taken by the processing unit 30 during the ping. Block 444 also represents that after each ping is completed, the transmitter(s) 82, 86 return to their previous deactivated operating state, with the processing unit 30 not providing any power to the transmitter(s) 82, 86 and/or providing a signal to the transmitter(s) 82, 86, preventing the transmitter(s) 82, 86 from emitting any ultrasonic signals necessary for the detection of air in the fluid delivery line 22. Thus, the processing unit effectively deactivates the air detection sensor after measuring the air content signals and after a second predetermined cycle parameter value has been met for each "ping," as shown by the combination of block A or 416 with block 444. Effectively, block A or 416 and associated blocks 412, 444 and 448 continue to execute through a plurality of pumping cycles, as long as the delivery is not complete and as long as an air in line alarm threshold has not been met. Thus, for each ping the processing unit 30 activates or reactivates the air detection sensor(s) 60, 90, 100 after a predetermined cycle parameter value has been met, such as a distance or time, as provided above. The medical pump 10 then measures an air content signal generated by the respective air detection sensor(s) 60, 90, 100 and generates air content data from the respective air content signal(s), in a similar manner as the detection of prior air content signal(s). The processing unit 30 then, again, determines whether the air content data (or air detection data) has met the predetermined air threshold, and deactivates the first air detection sensor(s) 60, 90, 100 after measuring the respective air content signal and after a respective predetermined cycle parameter value has been met, such as a distance or time.

Returning to block 428, as mentioned above, the processing unit 30 determines whether the air content data (or air detection data) has met the first predetermined air threshold, and in one embodiment, by determining whether "ADC" is greater than or equal to the ADC threshold. If the first predetermined air threshold is met, in one embodiment this represents that there is air in the fluid delivery line. If the first predetermined threshold is met, the flow moves to block 452. Block 452 represents processing unit 30 incrementing the air in line counter or "SAD." In one embodiment, the processing unit 30 increments the air in line counter or SAD by the stroke volume of one stoke of a pumping cycle divided by three. Of course, the stroke volume can vary depending on the pump and the cassette used, but in one embodiment the stroke volume is 75 uL so that the stroke volume divided by three is 25 uL. The flow then moves to block 456. Block 456 represents the processing unit 30 determining whether the air in line counter or SAD has met a "single" alarm threshold. In one embodiment, the determination includes determining whether the SAD is greater than or equal to the single alarm threshold. The alarm threshold is typically predetermined by the manufacturer at the factory and/or modified by a caregiver or biomedical engineer and/or can be configured as a downloadable drug library parameter that can be customized by the user for a particular clinical care area, pump type, pump software version, patient type (adult versus infant, for example), or drug. In one embodiment, the single alarm threshold can be selected by a caregiver from a group having at least the choices of 50 uL, 100 uL, 150 uL, 250 uL and 500 uL. In this embodiment, 50 uL is the lowest single alarm threshold that can be selected, and 250 uL is the default setting. Other values can be used as well.

If the determination at block 456 is true, the flow moves to block 460. Block 460 represents the processing unit 30 issuing a "single" air in line alarm in response to the SAD value being greater than the single alarm threshold in block 456. The flow then moves to block 464, which represents the processing unit 30 stopping the fluid delivery. Block 468 represents an interaction between the flow and blocks shown in FIG. 4 and FIG. 6 with the flow and blocks shown in FIG. 5, as will be described in more detail below.

In one embodiment described above, the processing unit 30 receives, stores in memory, and averages eight air content signals/data. Also as described above, the processing unit 30 can control the pump drive 38, 42 to cause the pump drive 38, 42 to rotate or drive at a speed based on the delivery rate set by the caregiver. The delivery rate and pump drive speed establish a stroke speed. However, in one embodiment, the number of samples measured, stored and/or averaged by processing unit 30 is independent of the stroke speed. Thus, the way in which the measurements are taken by the processing unit 30 and programming code 36 running therein, including the number of samples taken of the air content signal is not dependent on the speed of the fluid moving through the delivery line 22.

Figure 7:
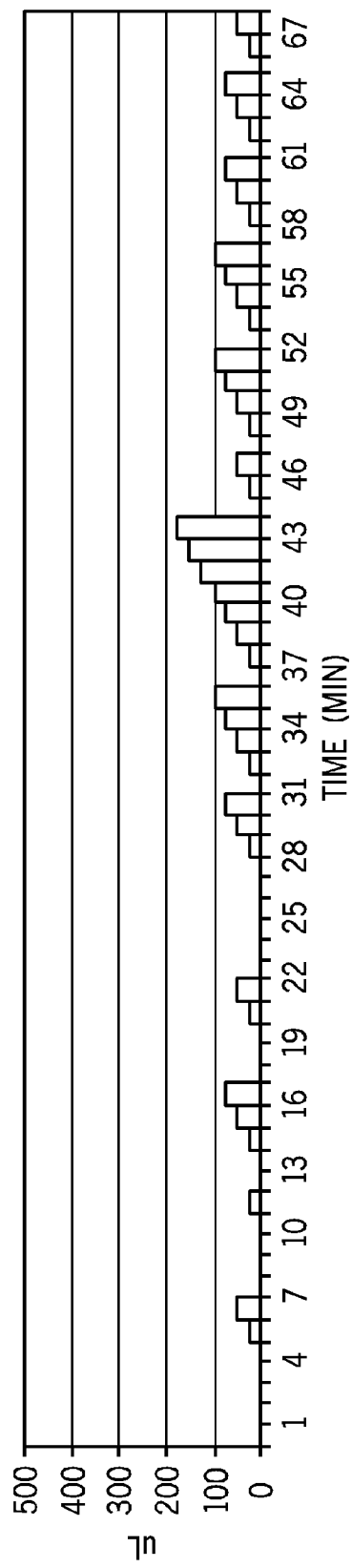
FIG. 7 is a graph of single air data over time from execution of the flow chart of FIG. 4.
Figure 8:
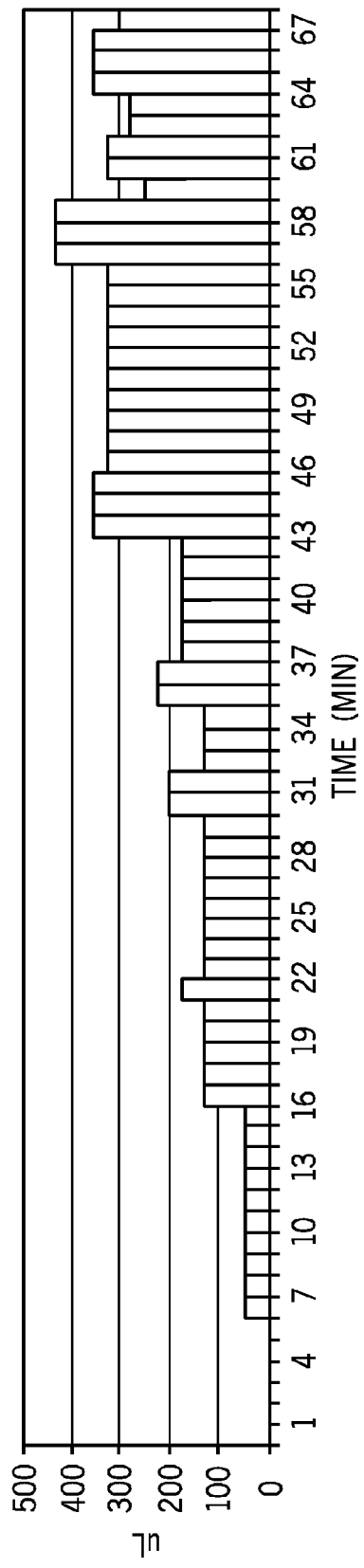
FIG. 8 is a graph of cumulative air data over time from execution of the flow chart of FIG. 5.

FIG. 5 shows a cumulative air in line detection flow diagram. Specifically, block 468 from FIG. 4 or FIG. 6 is the same as block 504 in FIG. 5, which indicates that the SAD or air in line counter data is used as input for additional determinations, as will now be described. It should be understood that the logic and flow of FIG. 4 and/or FIG. 6 can be taking place simultaneously with the logic and flow of FIG. 5, and vice versa. The flow moves to block 508, which represents that at the beginning of a fluid delivery a time parameter is equal to zero, at least theoretically. Instead of the time parameter being the number zero, a real time of day and date (Julian or otherwise) can be stored and used as a reference point, but which is otherwise theoretically considered as zero for the purposes of the method of the present invention. Reference should also be made to FIGS. 7 and 8 for charts which show SAD values generated by the processing unit 30 and stored in memory 34 over time, as well as "CAD" (Cumulative Air Data) values generated by the processing unit 30 and stored in memory 34 over time. Specifically, each time the above-determinations are made, the processing unit 30 will store another air in line counter value representing a "current" value of the air in line counter, which is proximate to each time the air content signal is measured and to each time the air content data is generated. Thus, a plurality of stored air in line counter values or plurality of SAD values is created and stored, and used as follows.

The flow then moves to block 512, which represents a continuous action by the processing unit 30 of finding the maximum "SAD" values for each string of non-zero SAD values. In other words, for each string of non-zero SAD values, having at least one SAD value as a part of such string, the processing unit 30 continuously determines the maximum value for the string, or string maximum SAD, of all such non-zero SAD values. The flow then moves to block 516, which represents that the string maximum SAD value must meet a minimum value in order to be considered relevant and be considered as a string maximum SAD. In the embodiment shown in FIG. 5, all string maximum SAD values must be at least fifty (50), otherwise such SAD value is ignored. If an SAD value is ignored, then the processing unit 30 unit does not use the SAD value in determining a Cumulative Air Data ("CAD") or a cumulative air in line counter value determination, described below. The flow next moves to block 520, which represents the processing unit 30 determining whether time elapsed since the fluid delivery began has met a predetermined cumulative time interval. In the embodiment shown in FIG. 5, the predetermined cumulative time interval is fifteen minutes, and thus, if the processing unit 30 determines that the elapsed time since the fluid delivery began is greater than fifteen minutes, then the flow moves to block 524. Otherwise, the flow moves to block 528, which represents the processing unit 30 determining the cumulative air in line counter value or CAD value. In one embodiment, the processing unit 30 determines the present cumulative air in line counter value (CAD) by adding all of the non-ignored, maximum air in line counter values (maximum SAD's) for each string (non-ignored and non-zero). At block 528, as opposed to block 524, the processing unit 30 uses SAD values generated and stored in the memory 34 since the beginning of the delivery, also considered as time zero, to determine the CAD values for each determination, as long as the time elapsed since the beginning of the delivery is less than fifteen (15) minutes, per block 520. On the contrary, at block 524, the processing unit 30 uses SAD values generated and stored in the memory 34 over a predetermined cumulative time interval, which in the embodiment shown in FIG. 5 is the last fifteen (15) minutes of the fluid delivery, to determine the CAD value for each determination after the first fifteen (15) minutes of the delivery has been exceeded, per block 520. Thus, when the fluid delivery cycle begins, the predetermined cumulative time interval effectively begins at the beginning of the fluid delivery cycle. Over time, the predetermined cumulative time interval shifts, with the oldest values dropping out when new "current" SAD and CAD values are determined and stored, in a "moving window" or first in/first out (FIFO) process.

The following chart shows one example of values for ADC, the increment for SAD, SAD, SAD filtered (for maximum SAD), ignore volume less than 50 uL volume (ignore all SAD filtered or maximum SAD values below fifty (50)), and CAD for each minute of one sixty-seven (67) minute fluid delivery. In one embodiment, when the processing unit has determined that SAD should be incremented, the amount to increment SAD is the stroke volume divided by three or SV/3. The values in the following chart assume a stroke volume of seventy-five (75) and an ADC threshold of 3335.

| Time (min) | ADC | Increment for SAD | SAD | SAD filtered | Ignore volume <50 uL | CAD |
|---|---|---|---|---|---|---|
| 0 | 1041 | 0 | 0 | | | 0 |
| 1 | 1029 | 0 | 0 | 0 | 0 | 0 |
| 2 | 1029 | 0 | 0 | 0 | 0 | 0 |
| 3 | 995 | 0 | 0 | 0 | 0 | 0 |
| 4 | 1032 | 0 | 0 | 0 | 0 | 0 |
| 5 | 3335 | 25 | 25 | 0 | 0 | 0 |
| 6 | 3350 | 25 | 50 | 50 | 50 | 50 |
| 7 | 1054 | 0 | 0 | 0 | 0 | 50 |
| 8 | 1074 | 0 | 0 | 0 | 0 | 50 |
| 9 | 1159 | 0 | 0 | 0 | 0 | 50 |
| 10 | 1159 | 0 | 0 | 0 | 0 | 50 |
| 11 | 3400 | 25 | 25 | 25 | 0 | 50 |
| 12 | 1078 | 0 | 0 | 0 | 0 | 50 |
| 13 | 1034 | 0 | 0 | 0 | 0 | 50 |
| 14 | 3450 | 25 | 25 | 0 | 0 | 50 |
| 15 | 3450 | 25 | 50 | 0 | 0 | 50 |
| 16 | 3500 | 25 | 75 | 75 | 75 | 125 |
| 17 | 1299 | 0 | 0 | 0 | 0 | 125 |
| 18 | 1299 | 0 | 0 | 0 | 0 | 125 |
| 19 | 1026 | 0 | 0 | 0 | 0 | 125 |
| 20 | 3340 | 25 | 25 | 0 | 0 | 125 |
| 21 | 3350 | 25 | 50 | 50 | 50 | 175 |
| 22 | 1041 | 0 | 0 | 0 | 0 | 125 |
| 23 | 1009 | 0 | 0 | 0 | 0 | 125 |
| 24 | 984 | 0 | 0 | 0 | 0 | 125 |
| 25 | 984 | 0 | 0 | 0 | 0 | 125 |
| 26 | 1033 | 0 | 0 | 0 | 0 | 125 |
| 27 | 1103 | 0 | 0 | 0 | 0 | 125 |
| 28 | 3550 | 25 | 25 | 0 | 0 | 125 |
| 29 | 3500 | 25 | 50 | 0 | 0 | 125 |
| 30 | 3550 | 25 | 75 | 75 | 75 | 200 |
| 31 | 3333 | 0 | 0 | 0 | 0 | 200 |
| 32 | 3600 | 25 | 25 | 0 | 0 | 125 |
| 33 | 3650 | 25 | 50 | 0 | 0 | 125 |
| 34 | 3650 | 25 | 75 | 0 | 0 | 125 |
| 35 | 3560 | 25 | 100 | 100 | 100 | 225 |
| 36 | 3333 | 0 | 0 | 0 | 0 | 225 |
| 37 | 3800 | 25 | 25 | 0 | 0 | 175 |
| 38 | 3800 | 25 | 50 | 0 | 0 | 175 |
| 39 | 3900 | 25 | 75 | 0 | 0 | 175 |
| 40 | 3910 | 25 | 100 | 0 | 0 | 175 |
| 41 | 3920 | 25 | 125 | 0 | 0 | 175 |
| 42 | 3930 | 25 | 150 | 0 | 0 | 175 |
| 43 | 3940 | 25 | 175 | 175 | 175 | 350 |
| 44 | 3333 | 0 | 0 | 0 | 0 | 350 |
| 45 | 3940 | 25 | 25 | 0 | 0 | 350 |
| 46 | 3940 | 25 | 50 | 50 | 50 | 325 |
| 47 | 3330 | 0 | 0 | 0 | 0 | 325 |
| 48 | 3940 | 25 | 25 | 0 | 0 | 325 |
| 49 | 3940 | 25 | 50 | 0 | 0 | 325 |
| 50 | 3940 | 25 | 75 | 0 | 0 | 325 |
| 51 | 3940 | 25 | 100 | 100 | 100 | 325 |
| 52 | 3333 | 0 | 0 | 0 | 0 | 325 |
| 53 | 3950 | 25 | 25 | 0 | 0 | 325 |
| 54 | 3950 | 25 | 50 | 0 | 0 | 325 |
| 55 | 3950 | 25 | 75 | 0 | 0 | 325 |
| 56 | 3950 | 25 | 100 | 100 | 100 | 425 |
| 57 | 3330 | 0 | 0 | 0 | 0 | 425 |
| 58 | 3950 | 25 | 25 | 0 | 0 | 425 |
| 59 | 3950 | 25 | 50 | 0 | 0 | 250 |
| 60 | 3950 | 25 | 75 | 75 | 75 | 325 |
| 61 | 3200 | 0 | 0 | 0 | 0 | 325 |
| 62 | 3950 | 25 | 25 | 0 | 0 | 275 |
| 63 | 3950 | 25 | 50 | 0 | 0 | 275 |
| 64 | 3950 | 25 | 75 | 75 | 75 | 350 |
| 65 | 3200 | 0 | 0 | 0 | 0 | 350 |
| 66 | 3965 | 25 | 25 | 0 | 0 | 350 |
| 67 | 3970 | 25 | 50 | 50 | 50 | 300 |

Referring to FIGS. 7 and 8, the SAD and CAD values from this example are shown in graphical form over time within these two figures, respectively.

Referring back to FIG. 5, after both blocks 524 and 528, the flow moves to block 532, which represents the processing unit 30 determining whether any one of the cumulative air in line counter values have met a cumulative air in line counter value threshold. In one embodiment, the cumulative air in line counter value threshold is set at one (1) milliliter (mL), and the processing unit 30 determines whether the current CAD value is greater than one (1) mL, as shown in FIG. 5. This threshold is a clinical requirement for an alarm to be issued. (As with the SAD single alarm threshold and other thresholds described herein, the cumulative air in line alarm threshold is typically predetermined by the manufacturer at the factory and/or modified by a caregiver or biomedical engineer and/or can be configured as a downloadable drug library parameter that can be customized by the user for a particular clinical care area, pump type, pump software version, patient type (adult versus infant, for example), or drug.) If this determination has been met, the flow moves to blocks 544 and 548, which represent the processing unit 30 issuing a cumulative air in line alarm and stopping the fluid delivery of the pump 10, respectively. If the current cumulative air in line counter value has not met the cumulative air in line counter value threshold, the flow then moves from block 532 to block 536, which represents the processing unit 30 determining whether the fluid delivery has been completed yet. If the processing unit 30 determines that the fluid delivery has been completed, then the flow moves to block 540, which represents the processing unit 30 stopping the fluid delivery of the pump 10. If the processing unit 30 determines that the fluid delivery has not been completed, then the flow moves to back to block 512 for continued cumulative air-in-line detection.

Referring to FIG. 6, a single air-in-line detection flow diagram is shown for a dual air detection sensor embodiment. The embodiment shown is FIG. 6 is specifically directed to a medical pump 10 of FIGS. 1 and 2 having a first air detection sensor 90 and a second air detection sensor 100, as shown in FIG. 2. The flow diagram of FIG. 6 generally follows the flow of FIG. 4, as specifically indicated by use of the same block numbering for those blocks which are the same in FIG. 6 as in FIG. 4. For all such blocks in FIG. 6 which are the same as the blocks in FIG. 4, it should be understood that functions which the processing unit 30, programming code 36, memory 34 and/or other components of the medical pump 10 perform in relation to the first air detection sensor 90, including the first transmitter 82 and first receiver 84, are also applicable to the second air detection sensor 100, including the second transmitter 86 and the second receiver 88, as suggested within the above description of FIG. 4. However, some of the functional blocks within the flow diagram of FIG. 6 include some different and additional functions, designated by a "prime" after the same block number as in FIG. 4 and/or a different block number, as shown. Specifically, block 416' represents a modified block "A" from FIG. 4 in that at least blocks 604 and 608 have been added between blocks 428 and 452. In addition, block 448' represents that the block 448 is performed in relation to both the first and second air detection sensors 90, 100, in addition to the other functional blocks being performed in relation to both first and second air detection sensors 90, 100.

Referring to block 428 in FIG. 6, similar to block 428 in FIG. 4, the processing unit 30 determines whether the air content data (or air detection data) has met the first predetermined air threshold, and in one embodiment, by determining whether "ADC" is greater than or equal to the ADC threshold. Generally, if the first predetermined air threshold is met, in one embodiment this represents that there is air in the fluid delivery line. However, in order to be sure that air is being detected in the embodiment shown in FIG. 6, instead of the flow next moving to block 452 if the first predetermined threshold is met, the flow moves to block 604.

After the first or other predetermined cycle parameter value has been met, the medical pump 10 measures an air content signal generated by the second air detection sensor 100. Similar to and in addition to the first air detection sensor 90, the processing unit 30 and programming code 36 running therein are configured to generate air content data from the air content signal generated by the second air detection sensor 100. The processing unit 30 is further configured to determine when the air content signal generated by the first air detection sensor 90 is measured to establish a first air detection time.

The processing unit 30 is also configured to determine when the air content signal generated by the second air detection sensor 100 is measured to establish a second air detection time. The processing unit 30 also determines whether the difference between the second detection time and the first detection time has met a predetermined delay time. Block 604 represents one embodiment of this determination. Specifically, the processing unit 30 determines whether the time when the second single air detection or "SAD" detection takes place minus the time when the first single air detection or "SAD" detection takes place is less than or equal to a predetermined delay time. In one embodiment, the predetermined delay time is dependent upon the fluid delivery line 22 size, a delivery rate, and/or a distance between the first air detection sensor 90 and the second air detection sensor 100. Specifically, in one embodiment, the predetermined delay time or $T_{delay}$ is the expected delay when a real air bubble goes through the first air detection sensor 90, then goes through the second air detection sensor 100. This delay time is calculated and varies based on the fluid delivery line 22 tubing size, the delivery rate and the distance between the air detection sensors 90, 100. Assuming the use of a cassette 12 that holds nominally 75 uL of fluid, in a fluid delivery line 22 of a macro bore tubing, 75 uL occupies a 0.583" segment of this type of tubing. Thus, at a delivery rate of 250 mL/hr, 75 uL is being delivered every 1.08 seconds (0.075 mL×3600 sec/250 mL=1.08 seconds). In other words, the speed of an air bubble is 0.583"/1.08 sec, which equals 0.54 inches/sec. Hence, for a distance of one (1) inch between the centers of each of the first and second air detection sensor 90, 100, an air bubble detected by the first detection sensor 90 should be seen by the second air detection sensor 90 in 1.85 seconds after the first air detection sensor 90 detects the air bubble (1"×1.08 sec/0.583"=1.85 sec). It should noted that a macro bore tube is likely the worst case in terms of time delay since it has the largest inner diameter and it will take longer for an air bubble to travel through such a the fluid delivery line 22. Thus, using macro bore tubing values within calculations is likely the safest set of assumption values within ongoing determinations.

The spacing of the air detection sensor pairs, 82/84, 86/88 from one another can be different distances. In particular, one way to determine and set this distance includes the following process. In order to "test" a potential distance value, a value can be selected which maintains the air detection sensors as a part of the pump, yet does not cause the pump housing or construction to become too large for commercial acceptability. This chosen distance or spacing value can be automatically fed back to the software to allow the pump to determine whether a true bubble is worth detecting. Specifically, for a given tube ID size, the air detection sensor pairs spacing, and delivery rate, the time at which a real bubble will pass through each sensor pair can be determined parametrically, as provided above with reference to FIG. 9 as well. In one commercially available pump made by the assignee of the present invention, dancing bubbles have been seen to oscillate within a 0.5" peak-to-peak range. Thus, a minimum spacing of 0.65" between the air sensor pairs should be observed to at least account for potential dancing bubbles. Failure to use this minimum spacing may void the design intent of adding extra sensors in series. A distance/spacing value between 0.75" and 1.0" would also be effective, since this spacing includes design margin as far as the "dancing bubble" coverage, and would still allow several air detection sensor pairs to be stacked, based on the minimal increase in size to the pump. Distances values higher than 1.0" can also be effective and commercially viable if pump size and costs associated therewith are not significantly increased as a result in the increased distance/spacing value.

If the determination of block 604 is met, the flow moves to block 608. In one embodiment, a tolerance value can be added to the process flow and programming code 36 to factor in changes in an air bubble between the first and second air detection sensors 90, 100. Specifically, $\epsilon$ is a tolerance that can be used to compare a specific air bubble detected by the first air detection sensor 90 and detected by the second air detection sensor 100. $\epsilon$ can be set at zero to look for an exact match between air bubbles detected by the first and second air detection sensors 90, 100. However, one fifth of the stroke volume is a preferable value to use to factor in potential changes in the air bubble between the two sensors 90, 100. Thus, as indicated in block 608, in one embodiment, the processing unit determines if the difference between the second detection data has met/not met a predetermined multi-sensor tolerance value.

In the embodiment shown in FIG. 6, when the predetermined delay time has been exceeded or when the predetermined multi-sensor tolerance value has been exceeded, at blocks 604 and 608, respectively, the flow moves to block 432. Again, at block 432, in one embodiment, the processing unit 30 is configured to set the air in line counter to zero. However, when the predetermined delay time has not been exceeded and when the predetermined multi-sensor tolerance value has not been exceeded, at blocks 604 and 608, respectively, the flow moves to block 452. Again, at block 452, the processing unit 30 is configured to increment the air in line counter, such by a stroke volume divided by three, similar to one prior embodiment. Likewise, the flow then moves to block 456. At block 456, the processing unit 30 determines whether the air in line counter has met the alarm threshold, and issues an air in line alarm when the alarm threshold has been met.

Similar to one prior embodiment, in the embodiment shown in FIG. 6, the processing unit 30 is further configured to deactivate both the first and second air detection sensors 90, 100 after measuring the first air content signals generated by the first and second air detection sensor 90, 100, as exemplified in block 444 by turning the first and second transmitters 82, 86, respectively, off. The sensors 90, 100 are turned off after each ping is complete, such as after a second predetermined cycle parameter value has been met. Likewise, at the beginning of each ping, the processing unit 30 reactivates the first and second sensors 90, 100, and further air content signals generated by the first and second air detection sensors 90, 100 are measured. The medical pump 10, such as through the processing unit 30, generates air content data or air content signals generated by the air detection sensors 90, 100 in the additional pings. After one or more additional predetermined cycle parameter values have been met, the processing unit 30 deactivates the air detection sensors 90, 100. The additional predetermined cycle parameter values cause the air content signals to be measured prior to the end of the pumping phase of the delivery cycle. Other features and aspects of the dual air detection sensor medical pump 10 embodiment can be understood with reference the single air detection sensor medical pump 10 and/or other portions of the present specification.

A skilled artisan should understand that the cumulative air in line detection flow shown and described in relation to FIG. 5 is applicable to single and multiple air detection sensor pump embodiments. Specifically, as SAD values are generated for each air detection sensor, CAD values are also generated for each air detection sensor. Thus, the SADs or air in line counter data for each air detection sensor, as suggested by blocks 604 and 608, are used as input for CAD/additional determinations. As previously mentioned, it should be understood that the logic and flow of FIG. 4 and/or FIG. 6 can be taking place simultaneously with the logic and flow of FIG. 5, and vice versa, for a multiple air detection sensor arrangement as well. Thus, for each air detection sensor the flow of FIG. 5 takes place. Thus, SAD values CAD values are generated by the processing unit 30 and stored in memory 34 over time. Specifically, each time the above-determinations are made for each air detection sensor, the processing unit 30 will store another air in line counter value representing a "current" value of the air in line counter, which is proximate to each time the air content signal is measured and to each time the air content data is generated. Thus, a plurality of stored air in line counter values or plurality of SAD values is created and stored, for each air detection sensor, and used in a similar manner as a single air detection sensor embodiment, but for each sensor.

Figure 9:
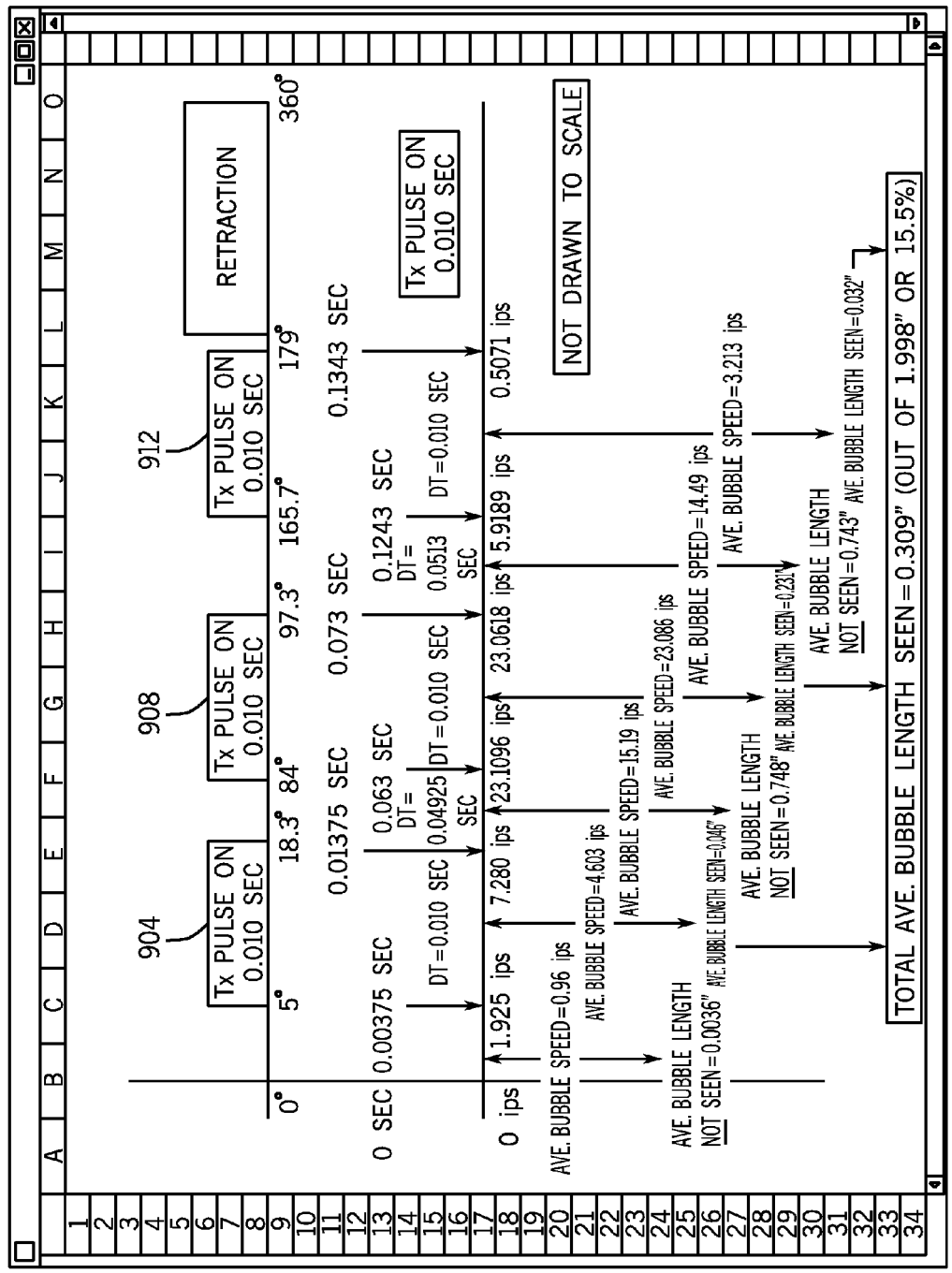
FIG. 9 is a timing diagram that may be useful in the determination and evaluation of one possible set of "pulses" or "pings" for one pumping cycle of the medical pump of the present invention.

With reference to at least FIG. 9, as briefly discussed above, a method can be used to determine where and for how long to place each "ping" for detecting air within the fluid delivery line. Within this method, one object is to make sure that there is enough air detection "coverage." To do so, a set of calculations can be performed to determine how fast a bubble of a particular size will travel through the fluid delivery line and to verify that a selected arrangement of one or more "pings" will "find" or detect the bubble based on the location of the bubble throughout the delivery phase of each stroke or cycle and the position and duration of each "ping.". In other words, there should be enough "pings" (one or more) for the appropriate length and appropriately spaced apart to reduce the risk/probability of outright missing air bubbles while at the same time reducing nuisance alarms. As one example, in a microbore tubing, a 75 uL bubble is about 1.998" long based on geometry of the tubing. At a delivery rate of 1000 mL/hr (which is the fastest delivery rate for one embodiment of a commercial pump of the assignee of the present invention), each delivery phase of a stroke (i.e. the time it takes for 75 uL to move down the tube) takes:

$$[(0.075 \text{ mL}/1000 \text{ mL}) \times 3600 \text{ sec}]/2 = 0.135 \text{ sec.}$$

In this equation, a divide by two (2) operation is needed to obtain the delivery phase time, which recognizes that half of the stroke is used for delivery and the other half is used to retract which doesn't involve fluid dispensing. Thus, 75 uL, on average, travels at a speed of:

$$1.998"/0.135 \text{ sec} = 14.8 \text{ ips (inches per second).}$$

In addition, at a delivery rate of 1000 mL/hr, a constant motor speed of 6000 RPM is used, which translates into a constant output shaft RPM of 222.22 in view of a gear reduction of 27 to 1. At 222.22 RPM, 1333.33 degrees of rotation per second is achieved. These calculations may be understood even better with reference to at least the disclosure within U.S. patent application Ser. No. 11/510,106, filed Aug. 25, 2006, entitled System And Method For Improved Low Flow Medical Pump Delivery.

Referring to the details of FIG. 9, a timing diagram of one set of "pulses" or "pings" for one pumping cycle or stroke of a medical pump 10, such as the medical pump 10 of FIG. 1 or 2 is shown. The information obtained and shown in FIG. 9 provides one example of where to place each of the pings, and the above and other calculations can be used to assess the ping placement arrangement shown therein. Specifically, first, second and third pings 904, 908 and 912, respectively, are shown. The first pulse 904 begins at 5 degrees after the beginning of the delivery portion of pumping cycle and ends at 18.3 degrees after the beginning of the delivery portion, in terms of angle of rotation of the pump drive. The second pulse 908 begins at 84 degrees after the beginning of the delivery portion and ends at 97.3 degrees after the beginning of the delivery portion, in terms of angle of rotation of the pump drive. The third pulse 912 begins at 165.7 degrees after the beginning of the delivery portion and ends at 179 degrees after the beginning of the delivery portion, in terms of angle of rotation of the pump drive.

The depiction in FIG. 9 does not factor in the pressurization phase of the pumping stroke. However, in a pump embodiment which includes a period of time in which movement of the fluid in the delivery line effectively stops, such as the pressurization phase within one embodiment of the present invention, this should be factored into the placement of the "pings." In a pump embodiment including a pressurization phase, the first ping 904 could take place after a predetermined angle of rotation, such as where there is high probability that the pressurization phase is complete (cracking has occurred) and such as at a position that will reduce the risk of missing an actual air bubble. Alternatively, the first ping can be placed at a predetermined angle or time after a calculated or determined end to the pressurization phase and beginning of the delivery phase.

Additional analytical information is provided within FIG. 9, which can be understood from at least some of the information provided above, and from the following. In one embodiment having a constant output shaft of 222.22 RPM, for an air bubble to travel from zero degrees to 0.5 degrees, it takes:

$$(0.5°-0°)/1333.33°/\text{sec}=0.000375 \text{ sec}.$$

At 0.5°, the plunger has moved down by 0.030"×(1−cosine (0.5°))=1.1423e-06 inch (where 0.030" is the nominal cam offset). This equation is based in part on information and calculations provided in U.S. patent application Ser. No. 11/510,106, filed Aug. 25, 2006, entitled System And Method For Improved Low Flow Medical Pump Delivery. The instantaneous plunger speed is defined as the total displacement divided by the total cumulative time and at 0.5°:

$$1.1423\text{e-}06 \text{ inch}/0.000375 \text{ sec}=0.003046 \text{ ips}$$

This can be translated into a linear position for the plunger, for each angle. If this calculation is performed for angles from 0° to 180°, the average plunger speed at 1000 mL/hr is about 0.44 ips. A speed ratio between the bubble and the plunger can be defined as K, and calculated as follows:

$$\text{average bubble speed/average plunger speed}=14.8 \text{ ips}/0.44 \text{ ips}=33.30$$

From these calculations, and based on the location and duration of the ping, a determination of how much bubble length is exposed to the ping can be performed, which assists in determining whether enough ping "coverage" exists. For example, in the first ping 904 in FIG. 9, which extends from 5° to 18.3°, the average bubble speed is about:

$$(1.925 \text{ ips}+7.280 \text{ ips})/2=4.603 \text{ ips}.$$

The 1.925 ips and 7.280 ips are determined for each of the respective degrees for the first ping, as shown in FIG. 9, using the calculations above. Since each ping 904, 908, 912 in FIG. 9 is turned ON for 0.010 sec, this translates into the following amount of a bubble being exposed to the first and subsequent pings:

$$(0.010 \text{ sec}\times 4.603 \text{ ips})=0.046"$$

Thus, one object is to select the ping locations and ON time so as to maximize the amount of bubble exposure to each ping. Preferably, one "ping" should be located where plunger and air bubble speed are at the highest value. As shown in FIG. 9, air bubble speed increases significantly toward the midpoint of the delivery phase of the pumping cycle. FIG. 9 specifically provides the air bubble speed at the beginning and end of each pulse 904, 908, 912, and provides an "average bubble speed" at the midpoint between each beginning and each end, and each end and each beginning, of each pulse 904, 908, 912. For each midpoint, FIG. 9 also shows the average bubble length by visual measurements taken at each of these points. This then translates into an amount of "average bubble length not seen" as well for each air detection sensor "OFF" interval and each air detection sensor "ON" interval. As shown, a total average bubble length seen can be determined. This information can further be used to determine whether the "tested" ping configuration has a low probability of not detecting one or more air bubbles.

It should be emphasized that the above-described embodiments of the present invention are examples of implementations, and are merely set forth for a clear understanding of the principles of the invention. Many variations and modifications may be made to the above-described embodiment(s) of the invention without substantially departing from the spirit and principles of the invention. All such modifications are intended to be included herein within the scope of this disclosure and by the following claims.

What is claimed is:

1. A medical pump for delivery of a substance through a fluid delivery line connected to a pumping chamber, comprising:
   a pump drive for exerting a force on the pumping chamber;
   a pump drive position sensor operatively connected to the pump drive for sensing the position of the pump drive;
   a first air detection sensor for sensing whether there is air in the fluid delivery line;
   a processor in electronic communication with the pump drive, the pump drive position sensor and the first air detection sensor;
   a memory in electronic communication with the processor, wherein the memory comprises programming code for execution by the processor, and wherein the programming code is adapted to:
   start a fluid delivery cycle having a pressurization phase, a delivery phase, and a retraction phase;
   activate the first air detection sensor, during one of a first pressurization phase and a first delivery phase, after a first predetermined cycle parameter value has been met;
   generate first air content data from a first air content signal measured by the first air detection sensor;
   determine whether the first air content data has met a first predetermined air threshold;
   deactivate the first air detection sensor, during one of the first pressurization phase and the first delivery phase, after the first air content signal is measured and after a second predetermined cycle parameter value has been met;
   reactivate the first air detection sensor, during one of the first pressurization phase and the first delivery phase, after a third predetermined cycle parameter value has been met;
   generate second air content data from a second air content signal measured by the first air detection sensor;
   determine whether the second air content data has met the first predetermined air threshold; and,
   deactivate the first air detection sensor, during one of the first pressurization phase and the first delivery phase, after the second air content signal is measured and after a fourth predetermined cycle parameter value has been met.

2. The medical pump of claim 1 wherein the programming code is further adapted to:
increment an air in line counter when the first predetermined threshold is met.

3. The medical pump of claim 2 wherein the programming code is further adapted to:
increment the air in line counter by a stroke volume divided by three when the first predetermined threshold is met.

4. The medical pump of claim 3 wherein the programming code is further adapted to:
determine whether the air in line counter has met an alarm threshold; and,
issue an air in line alarm when the alarm threshold has been met.

5. The medical pump of claim 1 wherein the programming code is adapted to:
increment an air in line counter when the first predetermined threshold is met;
set the air in line counter to zero when the first predetermined threshold is not met;
store in the memory an air in line counter value representing a current value of the air in line counter, proximate to each time that the step of measuring the first air content signal occurs, to create a plurality of stored air in line counter values;
determine whether each of the plurality of stored air in line counter values has met a first predetermined air in line counter threshold;
set to zero each of the plurality of stored air in line counter values that has not met the first predetermined air in line counter threshold;
determine a highest stored air in line counter value for each group of continuous non-zero stored air in line counter values;
establish a current cumulative air in line counter value for each group of continuous non-zero stored air in line counter values, wherein each cumulative air in line counter value is established by adding the highest stored air in line counter value to a previously determined cumulative air in line counter value;
determine if the current cumulative air in line counter value has met a cumulative air in line counter value threshold; and,
issue a cumulative air in line alarm if any one of the cumulative air in line counter values has met the cumulative air in line counter value.

6. The medical pump of claim 1, further comprising a second air detection sensor, wherein the programming code is further adapted to:
activate the second air detection sensor after the first predetermined cycle parameter value has been met;
measure a first air content signal generated by the second air detection sensor;
generate first air content data from the first air content signal generated by the second air detection sensor;
determine when the first air content signal generated by the first air detection sensor is measured to establish a first air detection time;
determine when the first air content signal generated by the second air detection sensor is measured to establish a second air detection time; and,
determine whether the difference between the second detection time and the first detection has met a predetermined delay time.

* * * * *